US010278624B2

(12) United States Patent
Short et al.

(10) Patent No.: US 10,278,624 B2
(45) Date of Patent: *May 7, 2019

(54) METHOD AND SYSTEM FOR MAINTAINING OR IMPROVING WELLNESS

(71) Applicant: iPhenotype LLC, San Diego, CA (US)

(72) Inventors: Jay M. Short, Del Mar, CA (US); Steve Briggs, Del Mar, CA (US)

(73) Assignee: IPHENOTYPE LLC, San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/892,187

(22) PCT Filed: May 23, 2014

(86) PCT No.: PCT/US2014/039286
§ 371 (c)(1),
(2) Date: Jan. 12, 2016

(87) PCT Pub. No.: WO2014/190234
PCT Pub. Date: Nov. 27, 2014

(65) Prior Publication Data
US 2016/0239624 A1    Aug. 18, 2016

Related U.S. Application Data

(63) Continuation of application No. PCT/US2013/042527, filed on May 23, 2013.

(60) Provisional application No. 61/909,378, filed on Nov. 27, 2013, provisional application No. 61/909,873, filed on Nov. 27, 2013, provisional application No. 61/909,386, filed on Nov. 27, 2013, provisional application No. 61/895,964, filed on Oct. 25, 2013, provisional application No. 61/895,969, filed on Oct. 25, 2013, provisional application No. 61/895,974, filed on Oct. 25, 2013.

(51) Int. Cl.

| | | |
|---|---|---|
| *A61B 5/00* | (2006.01) |
| *A61B 5/145* | (2006.01) |
| *G06F 16/28* | (2019.01) |
| *G06F 16/9535* | (2019.01) |
| *G06F 19/18* | (2011.01) |
| *G06Q 30/02* | (2012.01) |
| *G06Q 50/22* | (2018.01) |
| *A61B 3/113* | (2006.01) |
| *A61B 5/0205* | (2006.01) |
| *A61B 5/0488* | (2006.01) |
| *A61B 5/1459* | (2006.01) |
| *A61B 5/1473* | (2006.01) |
| *G09B 19/00* | (2006.01) |
| *A61B 5/16* | (2006.01) |
| *G06Q 30/06* | (2012.01) |
| *G09B 5/12* | (2006.01) |
| *G16H 10/20* | (2018.01) |
| *G16H 40/63* | (2018.01) |
| *G16H 50/70* | (2018.01) |
| *G06F 19/00* | (2018.01) |
| *G06F 19/24* | (2011.01) |
| *A61B 5/021* | (2006.01) |
| *A61B 5/024* | (2006.01) |
| *A61B 5/08* | (2006.01) |
| *A61B 5/05* | (2006.01) |

(52) U.S. Cl.
CPC .......... *A61B 5/14546* (2013.01); *A61B 3/113* (2013.01); *A61B 5/02055* (2013.01); *A61B 5/0488* (2013.01); *A61B 5/1459* (2013.01); *A61B 5/1473* (2013.01); *A61B 5/165* (2013.01); *A61B 5/4875* (2013.01); *A61B 5/7246* (2013.01); *G06F 16/285* (2019.01); *G06F 16/9535* (2019.01); *G06F 19/00* (2013.01); *G06F 19/18* (2013.01); *G06Q 30/02* (2013.01); *G06Q 30/0631* (2013.01); *G06Q 50/22* (2013.01); *G09B 5/12* (2013.01); *G09B 19/00* (2013.01); *G16H 10/20* (2018.01); *G16H 40/63* (2018.01); *G16H 50/70* (2018.01); *A61B 5/021* (2013.01); *A61B 5/024* (2013.01); *A61B 5/05* (2013.01); *A61B 5/0816* (2013.01); *G06F 19/24* (2013.01)

(58) Field of Classification Search
None
See application file for complete search history.

(56) References Cited

U.S. PATENT DOCUMENTS

| | | |
|---|---|---|
| 4,591,570 A | 5/1986 | Chang |
| 4,829,010 A | 5/1989 | Chang |
| (Continued) | | |

FOREIGN PATENT DOCUMENTS

| | | |
|---|---|---|
| EP | 1248213 A1 | 10/2002 |
| EP | 2390651 A1 | 11/2011 |
| (Continued) | | |

OTHER PUBLICATIONS

International Search Report; dated Sep. 25, 2014 for PCT Application No. PCT/US2014/039286.

(Continued)

*Primary Examiner* — Changhwa J Cheu
(74) *Attorney, Agent, or Firm* — Mendelsohn Dunleavy P.C.

(57) ABSTRACT

A method for providing a assistance for maintaining or improving an individual's wellness, comprising the steps of measuring a presence and/or concentration of one or more biomarkers in a sample from the individual; predicting a wellness need for maintaining or improving the individual's wellness based on the measured presence and/or concentration of the one or more biomarkers, wherein the one or more biomarkers are indicators of the wellness need; and altering the living environment of the individual, providing a wellness product or service to the individual or providing information, guidance or advice to the individual for addressing the wellness need of the individual. A system providing assistance for maintaining or improving an individual's wellness is also provided.

16 Claims, 2 Drawing Sheets

(56) References Cited

U.S. PATENT DOCUMENTS

| | | | |
|---|---|---|---|
| 5,100,777 A | 3/1992 | Chang | |
| 5,270,163 A | 12/1993 | Gold et al. | |
| 5,475,096 A | 12/1995 | Gold et al. | |
| 5,602,040 A * | 2/1997 | May | G01N 33/54366 422/401 |
| 6,797,522 B1 | 9/2004 | Still et al. | |
| 7,067,326 B2 | 6/2006 | Still et al. | |
| 8,008,020 B2 * | 8/2011 | Fung | G01N 33/6893 435/7.1 |
| 2003/0045827 A1 | 3/2003 | Nier et al. | |
| 2004/0019435 A1 | 1/2004 | Winfield et al. | |
| 2008/0033819 A1 | 2/2008 | Leschly | |
| 2010/0113892 A1 | 5/2010 | Kaput et al. | |
| 2010/0260739 A1 | 10/2010 | Short et al. | |
| 2011/0024309 A1 | 2/2011 | Lee | |
| 2011/0071051 A1 | 3/2011 | Halter et al. | |
| 2011/0093249 A1 | 4/2011 | Holmes et al. | |
| 2011/0230732 A1 | 9/2011 | Edman et al. | |
| 2011/0313790 A1 | 12/2011 | Yao | |
| 2012/0015368 A1 * | 1/2012 | Del Galdo | C12Q 1/6883 435/6.12 |
| 2012/0041778 A1 | 2/2012 | Kraft | |
| 2012/0072233 A1 | 3/2012 | Hanlon et al. | |
| 2012/0076390 A1 | 3/2012 | Potts et al. | |
| 2012/0130732 A1 | 5/2012 | Blander et al. | |
| 2012/0164127 A1 | 6/2012 | Short et al. | |
| 2012/0197534 A1 | 8/2012 | Kavusi et al. | |
| 2012/0203465 A1 | 8/2012 | Callewaert et al. | |
| 2012/0232520 A1 * | 9/2012 | Sloan | A61B 5/14532 604/504 |
| 2012/0258865 A1 | 10/2012 | Short et al. | |
| 2013/0078620 A1 | 3/2013 | Gandini et al. | |
| 2013/0122518 A1 | 5/2013 | Callewaert et al. | |
| 2013/0124218 A1 | 5/2013 | Masloski et al. | |
| 2013/0130933 A1 | 5/2013 | McDevitt et al. | |

FOREIGN PATENT DOCUMENTS

| | | |
|---|---|---|
| WO | WO2005064337 A1 | 7/2005 |
| WO | WO2008088288 A1 | 9/2005 |
| WO | WO2006059270 A2 | 6/2006 |
| WO | WO2007102629 A1 | 9/2007 |
| WO | WO200714649 A1 | 10/2007 |
| WO | WO2012075445 A2 | 10/2007 |
| WO | WO2010138975 A1 | 12/2010 |
| WO | WO2012018535 A2 | 2/2012 |
| WO | WO2012021714 A2 | 2/2012 |
| WO | WO2013009589 A1 | 1/2013 |
| WO | WO2013033359 A1 | 3/2013 |

OTHER PUBLICATIONS

Kandel, Denise B., et al. "Urine nicotine metabolites and smoking behavior in a multiracial/multiethnic national sample of young adults." American Journal of Epidemiology 165.8 (2007): 901-910.

Xia, Fan, et al. "Colorimetric detection of DNA, small molecules, proteins, and ions using unmodified gold nanoparticles and conjugated polyelectrolytes." PNAS 107.24 (2010): 10837-10841.

Van de Kant, Kim Dg, et al. "Early diagnosis of asthma in young children by using non-invasive biomarkers of airway inflammation and early lung function measurements: study protocol of a case-control study." BMC public health 9.1 (2009): 210.

Shalon, Dari, Stephen J. Smith, and Patrick O. Brown. "A DNA microarray system for analyzing complex DNA samples using two-color fluorescent probe hybridization." Genome research 6.7 (1996): 639-645.

Pease, A. Caviani, et al. "Light-generated oligonucleotide arrays for rapid DNA sequence analysis." Proceedings of the National Academy of Sciences 91.11 (1994): 5022-5026.

Corradi, Massimo, and Antonio Mutti. "Exhaled breath analysis: from occupational to respiratory medicine." Acta bio-medica: Atenei Parmensis 76.Suppl 2 (2005): 20.

"First Estimate of Total Viruses in Mammals," Infectious Disease, Sep. 3, 2013, 7 pages.

Arnold, Carrie. "Gut feelings: the future of psychiatry may be inside your stomach." The Verge 21 (2013).

Greenfieldboyce, N., "Fat Bacteria in Human Guts Tied to Obesity," Dec. 20, 2006; Retrieved from http://www.npr.org/templates/story/story.php?storyId=6654607.

European Search Report; dated Jan. 3, 2018 for EP Application No. EP14800690.1.

European Search Report; dated May 28, 2018 for EP Application No. 14800495.5.

* cited by examiner

METHOD AND SYSTEM FOR MAINTAINING OR IMPROVING WELLNESS

BACKGROUND OF THE INVENTION

1. Field of the Invention

The present invention is generally related to a method and system for maintaining or improving wellness of an individual. More particularly, the present invention is related to a method and system for maintaining and improving wellness of an individual by using biomarkers.

2. Description of the Related Technology

People with a higher quality of life generally have an enhanced state of wellness. When people achieve enhanced wellness, they are more productive in all phases of their life: home, work, relationships, etc. The overall sense of wellness also helps with preventing illness and therefore decreases the need for healthcare. Wellness is much more than merely physical health, exercise or nutrition. It is the full integration of states of physical, mental, and emotional well-being. Wellness, especially physical wellness, is developed through a combination of beneficial physical activities, optimized living environment and healthy eating habits.

However, the onset of industrialization and advancements of modern technologies have changed people's lifestyle dramatically. Large proportions of the world population are now only a supermarket or fast food chain away from a variety of over-the-counter calorie-dense meals. In addition, most people spend the majority of their waking hours in a sedentary position—either pursuing an office job, watching television, playing computer games, reading or socializing. Unfortunately, the human body is ill-fitted for such a "high calorie intake—low calorie expenditure" lifestyle. The abundance of serious metabolic disorders characteristic of modern societies (e.g. obesity, diabetes, metabolic syndrome, cardiovascular disease, etc.) reflects the detriments of the modern human's lifestyle.

According to the 2009 Global Health Risks report (WHO, 2009) four of the five leading global risks for mortality pertain to metabolic abnormalities, these being high blood pressure (accounting for 13% of mortalities), high blood glucose (6%), physical inactivity (6%) and being overweight or obese (5%). At the same time, six of the eight risk factors accounting for the majority (61%) of cardiovascular mortalities are symptomatic of the modern lifestyle (i.e. high blood pressure, high body mass index, high cholesterol, high blood glucose, low fruit and vegetable intake, and physical inactivity).

Maintaining or even improving wellness can contribute tremendously to the quality of life. Researchers have developed many approaches and systems for improving wellness. WO 2013/009589 discloses a personalized nutritional and wellness assistant system comprising at least one light source, at least one light detector, and at least one component for generating or storing at least one value of carbon dioxide production rate or at least one value of oxygen consumption rate from the detected signal. The system can take an individual's expired air to measure the carbon dioxide production rate and/or oxygen consumption rate. The system is capable of providing a user with continuous real-time feedback about his/her current nutritional state, energy uptake levels, energy expenditure levels, and energy balance. The system may be programmed to provide warning signals to a user whenever the user's personal energy balance went outside a desirable range, and/or motivational feedback to help the user stay within the specified range. The system may also provide the user with instantaneous advice regarding the most suitable food sources to eat at any given time.

EP 1 248 213 A1 discloses a health advising method and system for providing information about a person's health, which enables the person to manage his own health needs. The health advising method comprises steps of receiving an application from a user who seeks advice about health; and sending a question sheet about the user's life, a kit for storing blood, and a blood-collecting needle to the user by mail. When the question sheet about the user's life is filled in, the kit into which blood of the user has been dropped, and the blood-collecting needle is sent back, an operator analyzes the blood in the kit. The analysis results (such as albumin, C-reactive protein blood sugar, count of red blood cells, count of white blood cells) and the answers to the questions are saved in a morbid state analysis expert system. The morbid state analysis expert system creates advice for the user on the basis of the saved data and knowledge accumulated in a database. The advice may include medical advice, nutritional advice, and exercise advice.

US 2013/0122518 discloses a method for monitoring an individual's health. The method comprises the steps of collecting a sample from the individual; applying the sample to an assay panel for monitoring biomarkers for three common risk factors: inflammation, oxidative stress, and antioxidant activity; performing at least one inflammation monitoring test, at least one oxidative stress monitoring test, and at least one antioxidant activity monitoring test in the panel; and determining levels of biomarkers related to inflammation, oxidative stress, and antioxidant activity. The assay panel is capable of monitoring biomarkers in urine or blood by chemical or enzymatic reactions, as well as by the use of antibodies. The method further provides information to the individual regarding the individual's relative health and/or risk of developing one or more diseases.

US 2012/0197534 discloses a biomarker monitoring system including a communication network, a portable wellness device configured to form a communication link with the communication network, the portable wellness device including an electronic detector configured to detect at least one biomarker in a biologic sample, a first memory, a plurality of program instructions stored in the first memory, and a processing circuit operably connected to the first memory and configured to execute the program instructions to generate wellness data based upon detection of the at least one biomarker in the biologic sample, and a remote user interface operably connected to the communication network and configured to display wellness data indicative of the status of an immune system based on the detection of the biomarkers.

US 2013/0130933 discloses a method for assessing the health and wellness status of an individual comprising the steps of: a) collecting a sample from the individual; b) measuring a plurality of biomarkers in said sample to generate a plurality of biomarker levels; c) determining a wellness index of the individual based said biomarker levels. The wellness index may include 1) the individual's biomarker-based index for risk of developing or having a disease; 2) the individual's biomarker-based index for risk for death; and/or 3) the individual's biomarker-based index of wellness and longevity.

WO 2010/138975 discloses a system and method for motivating users to improve their wellness by utilizing complex event processing based on sensors and user-interaction data from users. The method comprises the steps of receiving sensor data and user-interaction data of a user being monitored; performing continuous analytics on the received sensor and user-interaction data over time to determine current and predicted future wellness states of the user using complex event processing with inference and predictive models; performing background analytics on the received sensor and user-interaction data along with previously received sensor and user-interaction data from the user and other users to update parameters of the inference and predictive models; generating a personalized intervention for the user using at least the determined current and predicted future wellness states when a triggering rule is satisfied to motivate the user toward a wellness goal of the user; and performing outcome analytics to investigate which interventions work for which users in order to optimize interventions over time. The sensors are used to collect raw data of the users, including activity data, fitness data, biometric parameters and biomarkers. The motivations may be another's successful experience, scoring the user's efforts toward a personal goal, social network influences and creating virtual competitions.

US 2013/0124218 discloses a system and method to encourage a user through social media to participate in health-improving activities and to engage in health-conscious behaviors, thereby improving their overall health condition. The method comprises the step of: providing a computing system comprising a processor, a data storage medium, and software. The software causes the computing system to: form a plurality of virtual teams based on team formation data stored in the data storage medium; and form one or more virtual challenges based on challenge formation data stored in the data storage medium; where a user competes as a member of at least one of the plurality of virtual teams in the one or more virtual challenges by sending data representing a tracked health condition of the user over an electronic network to the computing system.

The references discussed above fail to appreciate that biomarkers in a sample from an individual may be used directly to assist the individual, optionally in real-time to maintain or improve the individual's wellness. The present invention provides a method and system for maintaining or improving an individual's wellness based on measurements of a presence and/or concentration of one or more biomarkers in a sample from the individual. The invention provides individualized information, advice, or guidance for maintaining or improving wellness.

SUMMARY OF THE INVENTION

In one aspect, the present invention provides a method for providing assistance, optionally in real-time, for maintaining or improving an individual's wellness, comprising the steps of measuring a presence and/or concentration of one or more biomarkers in a sample from the individual; predicting a wellness need for maintaining or improving the individual's wellness based on the measured presence and/or concentration of the one or more biomarkers, wherein the one or more biomarkers are indicators of the wellness need; and altering the living environment of the individual or providing information, advice, or guidance to the individual for addressing the wellness need of the individual.

In another aspect, the method of the present invention measuring the presence and/or concentration of one or more biomarkers in a sample from an individual by using one or more biosensors.

In yet another aspect, the method of the present invention measures the presence and/or concentration of one or more biomarkers in a sample by using by one or more electrodes.

In yet another aspect, the method of the present invention measuring the presence and/or concentration of one or more biomarkers in a sample by using an array of recognition molecules selected from antibodies, aptamers, oligonucleotides and combinations thereof.

In yet another aspect, the method of the present invention has a measuring step comprising measuring one or more physiological parameters of the individual.

In yet another aspect, the method of the present invention provides information, advice, or guidance comprising a course of action that addresses a predicted wellness need.

In yet another aspect, the method of the present invention provides a suggestion of a product that addresses a predicted wellness need.

In yet another aspect, the method of the present invention provides a suggestion of a service that addresses a predicted wellness need.

In yet another aspect, the method of the present invention provides one or more promotions or coupons of a product or service that addresses a predicted wellness need.

In yet another aspect, the present invention provides a system for providing assistance, optionally in real-time, to an individual for maintaining or improving the individual's wellness, comprising a measuring device for measuring a presence and/or concentration of one or more biomarkers in a sample from the individual; a predictor for predicting a wellness need of the individual to maintain or improve the individual's wellness based on the measured presence and/or concentration of the one or more biomarkers, wherein the one or more biomarkers are indicators of the wellness need; a controller for altering the living environment of the individual or providing information, advice, or guidance to the individual addressing the wellness need of the individual; and a database for storing correlations between the presence and/or concentration of biomarkers and at least one wellness need.

In yet another aspect, the system of the present invention comprising a measuring device that is implanted in the individual.

DEFINITIONS

Figure 1:
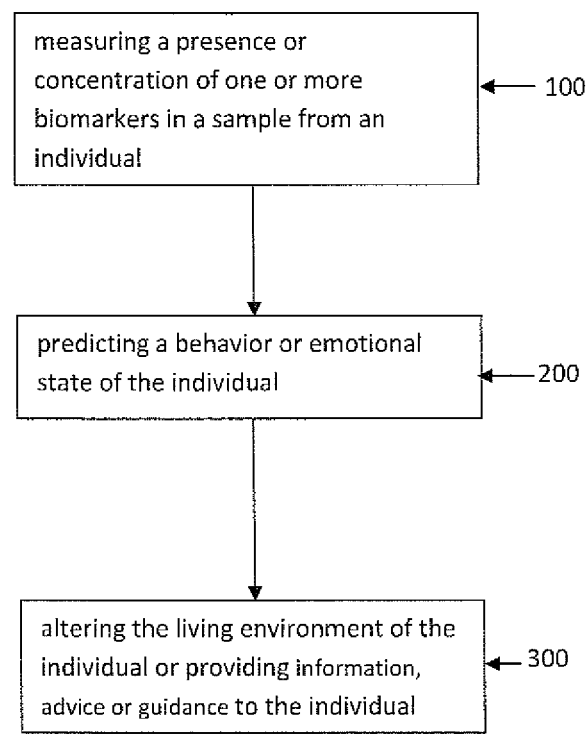
FIG. 1 is flow chart showing a method for providing assistance to an individual according to one embodiment of the present invention.

The term "sample" as used herein refers to bodily fluid or other materials taken from the body, including but not limited to saliva, sweat, blood, tears, mucus, urine, stool, mouth cell scrapings, breath, fart gas, hair follicle, fingernails, or other bodily cells. Samples can be collected by an individual breathing onto a surface, scraping a check, spitting into a tube, urinating into or onto a container or surface, or providing a sample in any other way whereby the sample can be collected for analysis, for example using a device.

The term "body fluid" as used herein refers any fluid that can be isolated from the body of an individual. For example, "body fluid" may include blood, plasma, serum, bile, saliva, urine, tears, perspiration, and the like. The body fluids of interest include fluids excreted by the body, such as urine, lacrimal fluid, sputum and nasal secretion, but also internal body fluids, such as lymph, synovial fluid (obtained by arthrocentesis) or cerebrospinal fluid (obtained by lumbar puncture).

The term "database" as used herein refers to an organized collection of data. The data are typically organized to model relevant aspects of reality in a way that supports processes requiring this information.

The term "phenotype" as used herein includes traits or characteristics that can be made visible by some technical procedure, and can include behavior as an observable characteristic. The phenotypes of the present invention may include biological phenotype, such as biological parameters on physical biological components of an individual and behavioral/emotional phenotype such as behaviors and emotional states of an individual.

As used herein, the term "assist" or "assistance" include providing information, feedback, guidance, or tailored or customized products, services, experiences, or environments.

As used herein, "behavior" includes lifestyle behavior, activities or actions that impact wellness, consumption activities, exercise, meditation, preferences, personality traits, and desires.

The term "biomarker" as used herein refers to a compound or molecule, or even a microbe, in a sample that has a predictive value for one or more wellness needs. Biomarkers may be, for example, polypeptides, polynucleotides (DNA and RNA), metabolites, microbes, inorganic compounds and ions. The presence, absence, reduction and/or upregulation of the biomarker may be associated with and/or be indicative of a particular disease or health concern. Determination of the level or activity of a biomarker in the sample may comprise the detection and quantification of the biomarker itself or of a precursor, derivative or metabolite thereof. A biomarker may also be associated with a specific state of a biological environment including but not limited to a phase of cellular cycle, or a health and disease state.

The term "biomolecule" as used herein indicates a substance compound or component associated to a biological environment including but not limited to sugars, amino acids, peptides, oligonucleotides, polynucleotides, polypeptides, organic molecules, haptens, epitopes, biological cells, parts of biological cells, vitamins, hormones and the like.

The term "polypeptide" as used herein refers to a polymer of amino acids joined by peptide bonds. The natural polypeptides are a long, continuous, and unbranched peptide chain. A polypeptide may be a protein, or fragments of a protein. A polypeptide may have one or more modifications, such as a post-translational modification (e.g., glycosylation, etc.) or any other modification (e.g., pegylation, etc.).

The term "proteome" as used herein is the entire set of proteins expressed by a genome, cell, tissue or organism at a certain time. More specifically, it is the set of expressed proteins in a given type of cell or organism, at a given time, under defined conditions.

The terms "polynucleotide," "nucleic acid" and "nucleic acid molecule" are used interchangeably herein to refer to a polymeric form of nucleotides of any length, and may comprise ribonucleotides, deoxyribonucleotides, analogs thereof, or mixtures thereof. This term refers only to the primary structure of the molecule. Thus, the term includes triple-, double- and single-stranded deoxyribonucleic acid ("DNA"), as well as triple-, double- and single-stranded ribonucleic acid ("RNA"). It also includes modified, for example by alkylation, and/or by capping, and unmodified forms of the polynucleotide. More particularly, the terms "polynucleotide," "oligonucleotide," "nucleic acid" and "nucleic acid molecule" include polydeoxyribonucleotides (containing 2-deoxy-D-ribose), polyribonucleotides (containing D-ribose), including tRNA, rRNA, hRNA, and mRNA, whether spliced or unspliced, any other type of polynucleotide which is an N- or C-glycoside of a purine or pyrimidine base.

The terms "nucleoside" and "nucleotide" as used herein include those moieties which contain not only the known purine and pyrimidine bases, but also other heterocyclic bases which have been modified. Such modifications include methylated purines or pyrimidines, acylated purines or pyrimidines, or other heterocycles. Modified nucleosides or nucleotides can also include modifications on the sugar moiety, e.g., wherein one or more of the hydroxyl groups are replaced with halogen, aliphatic groups, or are functionalized as ethers, amines, or the like. The term "nucleotidic unit" is intended to encompass nucleosides and nucleotides.

The term "microbes" as used herein includes virus, prokaryotic and eukaryotic microbial species from the Domains Archaea, Bacteria and Eucarya, the latter including yeast and filamentous fungi, protozoa, algae, or higher Protista. The terms "microbial cells" and "microorganism" are used interchangeably with the term "microbes."

The term "microflora" as used herein refers to a population of microbes in a specific localized location. Examples of microflora include the microbes in the stomach, the intestine, and microbes colonizing the outer surface of normal skin. Microflora do not pose a threat to the individual under normal circumstances, and do not cause infection. However, if one strain among the microflora becomes paramount, or if host resistance is reduced, or the epithelial surface broken, infection may supervene.

The term "lysis" or "lyse" as used herein refers to disrupting a cell (microbial cells or human cells) in order to gain access to materials inside of the cell that are otherwise inaccessible. Lysis generally causes the death of the cell by breaking of the cellular membrane and/or cell wall, which cause the contents of the cell to spill out. In particular, methods of lysis include, but are not limited to, chemical lysis, thermal lysis, mechanical lysis, and osmotic lysis. Lysis of cells or other biological samples is useful for analysis of such things as DNA, RNA, proteins or lipids. For example, one may wish to lyse a blood cell from a forensic blood sample in order assay the DNA of that cell. The term "lysate" as used herein indicates a liquid or solid collection of materials following a lysis procedure. The term "metabolite" as used herein refers to any substance produced during metabolism.

The term "metabolism" as used herein is defined as all chemical reactions involved in maintaining the living state of cells and the organism. Metabolism can be conveniently divided into two categories: catabolism which is the breakdown of molecules to obtain energy and anabolism which is the synthesis of all compounds needed by the cells. Metabolism is closely linked to nutrition and the availability of nutrients.

The term "aptamer" as used herein refers to a nucleic acid that has a specific binding affinity for a target molecule, such as a protein, polynucleotide or a small molecule (e.g. metabolite). An aptamer may be single or double-stranded nucleic acid (such as RNA or DNA) whose distinct nucleotide sequence determines the folding of the molecule into a unique three dimensional structure. Like all nucleic acids, a particular nucleic acid ligand may be described by a linear sequence of nucleotides (A, U, T, C and G), typically 15-40 nucleotides long.

The term "aptamer-based sensor" as used herein refers to a sensor on which the binding of a target may emit a signal detectable through spectroscopic detection techniques such as surface enhanced spectroscopy.

The term "surface enhanced spectroscopy" as used herein indicates signal enhancement techniques where signal detection from corresponding spectroscopic probes is performed in connection with a metal surface. Exemplary spectroscopic techniques suitable to detect aptamers include Surface-Enhanced Resonance Raman Spectroscopy (SERRS), Surface-Enhanced Raman Spectroscopy (SERS), Surface-Enhanced Fluorescence (SEF), Surface-Enhanced Infrared Absorption (SEIRA), Surface-Enhanced Hyper-Raman Scattering (SEHRS), Surface-Enhanced Coherent Anti-Stokes Raman Scattering (SECARS), and additional techniques identifiable by a skilled person.

The term "array" as used herein includes any one-dimensional, two-dimensional or substantially two-dimensional (as well as a three-dimensional) arrangement of addressable regions bearing a particular chemical moiety or moieties (such as ligands, e.g., biopolymers such as polynucleotide or oligonucleotide sequences (nucleic acids), polypeptides (e.g., proteins or antibodies), carbohydrates, lipids, aptamers, etc.) associated with that region. In many embodiments of interest, the arrays are arrays of nucleic acids, including oligonucleotides, polynucleotides, cDNAs, mRNAs, synthetic mimetics thereof, and the like. Where the arrays are arrays of oligonucleotides, the oligonucleotides may be covalently attached to the arrays at any point along the nucleic acid chain. In some embodiments, the oligonucleotides are attached at one of their termini (e.g. the 3' or 5' terminus). In some embodiments, arrays may comprise a plurality of antibodies, and/or aptamers which selectively bind to molecules (e.g., polynucleotides, polypeptides, metabolites) in a sample.

The term "microarray" as used herein refers to polynucleotide, polypeptide, aptamer and chemical microarrays. Specific polynucleotides, polypeptides, antibodies, small molecule compounds, aptamer, peptides, and carbohydrates may be immobilized on solid surfaces to form microarrays. Microarrays may be used to detect polynucleotides, polypeptides and other chemicals in a sample.

The term "specific" "specifically" or "specificity" as used herein used in reference to the binding of a first molecule to a second molecule refers to the recognition, contact and formation of a stable complex between the first molecule and the second molecule, together with substantially less to no recognition, contact and formation of a stable complex between each of the first molecule and the second molecule with other molecules that may be present. Examples of specific binding include antibody-antigen interactions, cellular receptor-ligand interactions, polynucleotide hybridization, enzyme substrate interactions, etc. The term "specific" as used herein with reference to a molecular component of a complex, refers to the unique association of that component to the specific complex which the component is part of. The term "specific" as used herein with reference to a sequence of a polynucleotide refers to the unique association of the sequence with a single polynucleotide which is the complementary sequence. By "stable complex" is meant a complex that is detectable and does not require any arbitrary level of stability, although greater stability is generally preferred.

The term "antibody", as used herein, refers to intact immunoglobulin molecules, as well as fragments of immunoglobulin molecules, such as Fab, Fab', (Fab')2, Fv, and SCA fragments, that are capable of binding to an epitope of an antigen. These antibody fragments, which retain some ability to selectively bind to an antigen (e.g., a polypeptide antigen) of the antibody from which they are derived, can be made using well known methods in the art (see, e.g., Harlow and Lane, supra), and are described further, as follows. Antibodies can be used to isolate preparative quantities of the antigen by immunoaffinity chromatography. Various other uses of such antibodies are to diagnose and/or stage disease (e.g., neoplasia) and for therapeutic application to treat disease, such as for example: neoplasia, autoimmune disease, AIDS, cardiovascular disease, infections, and the like.

An Fab fragment consists of a monovalent antigen-binding fragment of an antibody molecule, and can be produced by digestion of a whole antibody molecule with the enzyme papain, to yield a fragment consisting of an intact light chain and a portion of a heavy chain.

An Fab' fragment of an antibody molecule can be obtained by treating a whole antibody molecule with pepsin, followed by reduction, to yield a molecule consisting of an intact light chain and a portion of a heavy chain. Two Fab' fragments are obtained per antibody molecule treated in this manner.

An (Fab')2 fragment of an antibody can be obtained by treating a whole antibody molecule with the enzyme pepsin, without subsequent reduction. A (Fab')2 fragment is a dimer of two Fab' fragments, held together by two disulfide bonds.

An Fv fragment is defined as a genetically engineered fragment containing the variable region of a light chain and the variable region of a heavy chain expressed as two chains.

The term "conditionally active antibody" as used herein refers to a variant, or mutant, of a wild-type antibody which is more or less active than the parent wild-type antibody under one or more normal physiological conditions. This conditionally active antibody also exhibits activity in selected regions of the body and/or exhibits increased or decreased activity under aberrant, or permissive, physiological conditions. Normal physiological conditions are those of temperature, pH, osmotic pressure, osmolality, oxidation and electrolyte concentration which would be considered within a normal range at the site of administration, or at the tissue or organ at the site of action, to a subject. An aberrant condition is that which deviates from the normally acceptable range for that condition. In one aspect, the conditionally active antibody is virtually inactive at wild-type conditions but is active at other than wild-type conditions at a level that is equal or better than at wild-type conditions. For example, in one aspect, a conditionally active antibody is virtually inactive at body temperature, but is active at lower temperatures. In another example, a conditionally active antibody is virtually inactive at a higher temperature, but is active at a lower temperature. In another aspect, the conditionally active antibody is reversibly or irreversibly inactivated at the wild type conditions. In another aspect, the conditionally active biologic protein is used as a drug, or therapeutic agent. In yet another aspect, the antibody is more or less active in abnormal pH (high pH or low pH). Conditionally active antibodies and methods of generating them are described in, for example, US 2012/0258865, US 2012/0164127, and US 2010/0260739, which are incorporated by reference herein in their entirety.

The term "single-chain antibody" as used herein refers to a polypeptide comprising a VH domain and a VL domain in polypeptide linkage, generally liked via a spacer peptide (e.g., [Gly-Gly-Gly-Gly-Ser]x), and which may comprise additional amino acid sequences at the amino- and/or carboxy-termini. For example, a single-chain antibody may comprise a tether segment for linking to the encoding polynucleotide. As an example a scFv is a single-chain antibody. Single-chain antibodies are generally proteins consisting of one or more polypeptide segments of at least 10 contiguous amino substantially encoded by genes of the immunoglobulin superfamily (e.g., see Williams and Barclay, 1989, pp. 361-368, which is incorporated herein by reference), most frequently encoded by a rodent, non-human primate, avian, porcine bovine, ovine, goat, or human heavy chain or light chain gene sequence. A functional single-chain antibody generally contains a sufficient portion of an immunoglobulin superfamily gene product so as to retain the property of binding to a specific target molecule, typically a receptor or antigen (epitope).

The term "amino acid" as used herein refers to any organic compound that contains an amino group (—NH$_2$) and a carboxyl group (—COOH); preferably either as free groups or alternatively after condensation as part of peptide bonds. The "twenty naturally encoded polypeptide-forming alpha-amino acids" are understood in the art and refer to: alanine (ala or A), arginine (arg or R), asparagine (asn or N), aspartic acid (asp or D), cysteine (cys or C), gluatamic acid (glu or E), glutamine (gin or Q), glycine (gly or G), histidine (his or H), isoleucine (ile or I), leucine (leu or L), lysine (lys or K), methionine (met or M), phenylalanine (phe or F), proline (pro or P), serine (ser or S), threonine (thr or T), tryptophan (trp or W), tyrosine (tyr or Y), and valine (val or V).

The term "amplification" as used herein refers that the number of copies of a polynucleotide is increased.

The term "polymerase chain reaction (PCR)" as used herein refers to a system for in vitro amplification of DNA. Two synthetic oligonucleotide primers, which are complementary to two regions of the target DNA (one for each strand) to be amplified, are added to the target DNA (that need not be pure), in the presence of excess deoxynucleotides and a heat-stable DNA polymerase, e.g., Taq DNA polymerase. In a series, e.g., 30, of temperature cycles, the target DNA is repeatedly denatured (e.g., around 90° C.), annealed to the primers (e.g., at 50-60° C.) and a daughter strand extended from the primers (e.g., 72° C.). As the daughter strands themselves act as templates for subsequent cycles, DNA fragments matching both primers are amplified exponentially, rather than linearly. The original DNA need thus be neither pure nor abundant, and the PCR reaction has accordingly become widely used not only in research, but in clinical diagnostics and forensic science.

The term "primer" as used herein refers to an oligonucleotide that hybridizes to a target sequence, typically to prime the nucleic acid in the amplification process.

The term "nested PCR" as used herein refers to a PCR in which specificity is improved by using two sets of primers sequentially. An initial PCR is performed with the "outer" primer pairs, then a small aliquot is used as a template for a second round of PCR with the "inner" primer pair.

The term "reverse transcription PCR or RT-PCR" as used herein refers to PCR in which the starting template is RNA, implying the need for an initial reverse transcriptase step to make a DNA template. Some thermostable polymerases have appreciable reverse transcriptase activity; however, it is more common to perform an explicit reverse transcription, inactivate the reverse transcriptase or purify the product, and proceed to a separate conventional PCR.

The term "digestion of DNA" as used herein refers to catalytic cleavage of the DNA with a restriction enzyme that acts only at certain sequences in the DNA. The various restriction enzymes used herein are commercially available and their reaction conditions, cofactors and other requirements were used as would be known to the ordinarily skilled artisan. For analytical purposes, typically 1 µg of plasmid or DNA fragment is used with about 2 units of enzyme in about 20 µl of buffer solution. For the purpose of isolating DNA fragments for plasmid construction, typically 5 to 50 µg of DNA are digested with 20 to 250 units of enzyme in a larger volume. Appropriate buffers and substrate amounts for particular restriction enzymes are specified by the manufacturer. Incubation times of about 1 hour at 37° C. are ordinarily used, but may vary in accordance with the supplier's instructions. After digestion the reaction is electrophoresed directly on a gel to isolate the desired fragment.

The term "oligonucleotide" (or synonymously an "oligo") as used herein refers to either a single stranded polydeoxynucleotide or two complementary polydeoxynucleotide strands which may be chemically synthesized. Such synthetic oligonucleotides may or may not have a 5' phosphate. Those that do not will not ligate to another oligonucleotide without adding a phosphate with an ATP in the presence of a kinase. A synthetic oligonucleotide will ligate to a fragment that has not been dephosphorylated. To achieve polymerase-based amplification (such as with PCR), a "32-fold degenerate oligonucleotide that is comprised of, in series, at least a first homologous sequence, a degenerate N,N,G/T sequence, and a second homologous sequence" is mentioned. As used in this context, "homologous" is in reference to homology between the oligo and the parental polynucleotide that is subjected to the polymerase-based amplification.

An oligonucleotide comprising at least 10, preferably at least 15, and more preferably at least 20 nucleotides, preferably no more than 100 nucleotides, can be hybridizable to a genomic DNA molecule, a cDNA molecule, or an mRNA molecule encoding a gene, mRNA, cDNA, or other nucleic acid of interest. Oligonucleotides can be labeled, e.g., with 32P-nucleotides or nucleotides to which a label, such as biotin, has been covalently conjugated. In one embodiment, a labeled oligonucleotide can be used as a probe to detect the presence of a nucleic acid. In another embodiment, oligonucleotides (one or both of which may be labeled) can be used as PCR primers. Generally, oligonucleotides are prepared synthetically, preferably on a nucleic acid synthesizer. Accordingly, oligonucleotides can be prepared with non-naturally occurring phosphoester analog bonds, such as thioester bonds, etc.

The term "nucleic acid probe" as used herein refers to a structure comprising a polynucleotide as defined above that contains a nucleic acid sequence that can bind to a corresponding target. The polynucleotide regions of probes may be composed of DNA, and/or RNA, and/or synthetic nucleotide analogs.

The term "sequence identity" as used herein means that two polynucleotide sequences are identical (i.e., on a nucleotide-by-nucleotide basis) over the window of comparison. The term "percentage of sequence identity" is calculated by comparing two optimally aligned sequences over the window of comparison, determining the number of positions at which the identical nucleic acid base (e.g., A, T, C, G, U, or I) occurs in both sequences to yield the number of matched positions, dividing the number of matched positions by the total number of positions in the window of comparison (i.e., the window size), and multiplying the result by 100 to yield the percentage of sequence identity. This "substantial identity", as used herein, denotes a characteristic of a polynucleotide sequence, wherein the polynucleotide comprises a sequence having at least 80 percent sequence identity, preferably at least 85 percent identity, often 90 to 95 percent sequence identity, and most commonly at least 99 percent sequence identity as compared to a reference sequence of a comparison window of at least 25-50 nucleotides, wherein the percentage of sequence identity is calculated by comparing the reference sequence to the polynucleotide sequence which may include deletions or additions which total 20 percent or less of the reference sequence over the window of comparison.

The term "complementary or matched" as used herein means that two nucleic acid sequences have at least 50% sequence identity. Preferably, the two nucleic acid sequences have at least 60%, 70%, 80%, 90%, 95%, 96%, 97%, 98%, 99% or 100% of sequence identity. "Complementary or matched" also means that two nucleic acid sequences can hybridize under low, middle and/or high stringency condition(s). The percentage of sequence identity or homology is calculated by comparing one to another when aligned to corresponding portions of the reference sequence.

The members of a pair of molecules (e.g., an antibody-antigen pair or a nucleic acid pair) are said to "specifically bind" to each other if they bind to each other with greater affinity than to other, non-specific molecules. For example, an antibody raised against an antigen to which it binds more efficiently than to a nonspecific protein can be described as specifically binding to the antigen. (Similarly, a nucleic acid probe can be described as specifically binding to a nucleic acid target if it forms a specific duplex with the target by base pairing interactions (see above)).

The term "specific hybridization" as used herein refers to the formation of hybrids between a first polynucleotide and a second polynucleotide (e.g., the second polynucleotide having a sequence substantially complementary to the sequence of the first polynucleotide), wherein substantially unrelated polynucleotide sequences do not form hybrids in the mixture.

The term "assay" as used herein refers to a measurement to quantify or qualify a component of a sample, preferably a protein, peptide, hormone, or other biological molecule.

The term "detect" or "detection" as used herein refers to the determination of the existence, presence or fact of a target or signal in a limited portion of space, including but not limited to a sample, a reaction mixture, a molecular complex and a substrate including a platform and an array. Detection is "quantitative" when it refers, relates to, or involves the measurement of quantity or amount of the target or signal (also referred as quantitation), which includes but is not limited to any analysis designed to determine the amounts or proportions of the target or signal. Detection is "qualitative" when it refers, relates to, or involves identification of a quality or kind of the target or signal in terms of relative abundance to another target or signal, which is not quantified. An "optical detection" indicates detection performed through visually detectable signals: spectra or images from a target of interest or a probe attached to the target.

The term "biosensor" as used herein refers to a sensor which converts an interaction between a target and a recognition molecule into a signal such as an electric signal, so as to measure or detect a target. The conventional biosensor is comprised of a receptor site for recognizing a chemical substance as a detection target and a transducer site for converting a physical change or chemical change generated at the site into an electric signal. In a living body, there exist substances having an affinity with each other, such as enzyme/substrate, enzyme/coenzyme, antigen/antibody, aptamer/ligand, or hormone/receptor. The biosensor operates on the principle that a substance having an affinity with a receiving molecule, as described above, is immobilized on a substrate to be used as a molecule-recognizing substance, so that the corresponding substance can be selectively measured.

The term "recognition molecules" as used herein refers to a molecule that is capable of specifically recognize and bind to a biomarker. Examples of recognition molecule-target pairs include receptor-ligand, antigen-antibody, enzyme-substrate, sugar-lectin. In addition, biomimetic molecules such as a synthetic receptor that can recognize a biomarker. Synthetic receptors are discussed in more details in U.S. Pat. Nos. 7,067,326, and 6,797,522 which are incorporated herein by reference in its entirety. Aptamer may also be used as a recognition molecule.

The term "receptor" as used herein refers to a protein embedded in either the cell's plasma membrane (cell surface receptors), in the cytoplasm, or in the cell's nucleus (nuclear receptors), to which specific molecules may bind. A molecule that binds to a receptor is called a ligand, and can be a peptide (short protein) or another small molecule such as a neurotransmitter, hormone, pharmaceutical drug, or toxin.

The term "aptamer-based sensor," "aptasensor," or "aptamer beacon" used herein refers to a sensor that can be used to capture a target exploiting the affinity of an aptamer to the target and that can be detected using techniques identifiable by a skilled person upon reading of the present disclosure.

The terms "implantable device" or "implant" as used herein refers to a device that has sufficient mechanical strength, conformability to anatomical surfaces, and suitable for implanting inside of a human body. Known implantable devices include shunts, intravenous catheters and/or arterial catheters, drug administration devices such as infusion pumps and the like.

The term "patch" as used herein includes any product having a pressure-sensitive adhesive surface that may be placed on the skin. Such products can be provided in various sizes and configurations, including tapes, bandages, sheets, plasters, and the like.

The term "strap" as used herein refers to any flexible belt, webbing, chain, rope or the like that is passed through the slot and doubled upon itself as a loop for securing it to any part of human body.

The term "wellness" as used herein refers any actual or perceived improved state of being including emotional, health, fitness, psychological, beauty, youth, confidence and desire as compared to a comparative state of being of a person. This is not the traditional model of health where wellness is determined merely by the absence of a disease or infirmity. Wellness in the context of the present invention is an improved state of functioning of an individual regardless of the individual's current health status or disability. Thus, wellness exists on a continuum and is unique to each individual person based on the individual's unique circumstances. Wellness may also be viewed as a holistic concept that looks at the individual as a whole and not just at the individual's blood pressure level or how much the individual weighs, or how well the individual manages stress.

Many factors may affect an individual's wellness. Some of these factors include pain management, social contribution, rest, consumer knowledge, exercise, personal growth and development, nutrition, health management, body weight, social support, skin care, employment, school, bodily functioning, accessibility accommodation, sexuality, personal assistant services, aging, housing, attitude, transportation, identity, knowledge and sensitivity of others, including health care providers, beliefs, alternative/complementary medicine, and self-determination.

The term "quality of life" as used herein refers to the ability to enjoy normal life activities; in general, a desirable state that includes happiness, wellness, stamina, drive, feeling of well being, comfort, as well as freedom from pain, anxiety, depression, and/or anger.

The term "susceptibility" as used herein refers to both determining whether any existing events or symptoms associated with or indicative of a mental or physical disorder experienced by an individual are linked to abnormal biomarker levels as described herein and to determining whether individuals who have not experienced events or symptoms indicative of a mental or physical disorder nevertheless exhibit a predisposition or risk thereto. Thus, depending on the particular circumstances of a particular individual the term "susceptibility" should be understood to mean vulnerability to a mental or physical disorder or having an increased likelihood of development of a mental or physical disorder in the future.

The term "treatment" as used herein refers to any and all treatments which remedy a disorder or one or more symptoms of a disorder, prevent the establishment of a disorder, provide early intervention for a disorder, provide management of residual symptoms of a disorder, prevent relapse of a disorder, overcome treatment resistance in a disorder, or otherwise prevent, hinder, retard, or reverse the progression of, or other undesirable symptoms of, a disorder in any way whatsoever. Thus the term "treatment" is to be considered in its broadest context. For example, treatment does not necessarily imply that a patient is treated until total recovery. Rather, "treatment" encompasses reducing the severity of, or delaying the onset of, a particular disorder. In the context of some disorders, methods of the present invention involve "treating" the disorder in terms of reducing or ameliorating the occurrence of a highly undesirable event associated with the disorder or an irreversible outcome of the progression of the disorder but may not of itself prevent the initial occurrence of the event or outcome. Accordingly, treatment includes amelioration of the symptoms of a particular disorder or preventing or otherwise reducing the risk of developing a particular disorder.

The term "severity" as used herein refers to the degree of symptom intensity experienced, ascertained, formally assessed or reported by a symptomatic subject with a mental or physical disorder.

The term "disease control" as used herein means the status of the disease or disorder, typically in light of intervention to treat the disease or disorder. Thus, "disease control" describes the range and severity of symptoms and conditions experienced and suffered by patients as a result of their disorder. Disease control effectively provides a measure at a given point in time of the disease status of an individual, reflecting both current therapeutic treatment regimes used by the individual and the individual's recent experiences and psychological state.

The term "mental disorder" as used herein refers generally to mild and severe mental illness health conditions, such as psychiatric or neuropsychiatric diseases, mood disorders, psychotic disorders, personality disorders, pre- and post-traumatic stress disorders, anxiety disorders, developmental disorders, learning disorders, sensory processing disorders, movement disorders, memory disorders, and behavioral disorders as well as other mental disorders and diseases. The disorder or condition may be one that requires or is amenable to intervention in the form of either drug administration or other medical, psychological or psychiatric treatment, but this need not be the case.

An individual "at risk for", "predisposed to", or "susceptible to" a disease or condition means that the risk for the individual to contract or develop the disease or condition is higher than in the average population.

As used herein, the terms "prevent," "preventing," and "prevention" refer to the prevention of the recurrence, onset, or development of a disorder or one or more symptoms thereof in a subject resulting from interventions.

As used herein, the terms "subject" and "subjects" refer to a human.

The term "promotion" or "offer" as used herein means providing any type of information in any language or translated into any language or scripting social media content in any language or translated into any language relating to any product or service for the purpose of promoting that product or service, and includes, but is not limited to, any type of advertisement, advertising, marketing, coupon, discount, offer, daily deal, auction used for promotion or offer, and the like.

The term "online promotion(s)" as used herein refers to any type of promotion or offer in any form provided over the Internet, such as a social network or website, blog, pop up and the like, including mobile or wireless devices, as well as any Internet accessing device, including any type of computing device or computer.

The term "product" as used herein refers to any product described herein, or as known in the art: non-limiting examples of products include, but are not limited to: merchandise, retail products, wholesale products, virtual products, electronics, clothing, food, water, beverages, commercial products, household or housing products, cleaning products, footwear, appliances, autos, trucks, motorcycles, boats, airplanes, commercial and residential construction products, music, audio, and video products, books, computers, hardware, systems, operating systems, software, products relating to mobile banking and mobile wallet services, products relating to entertainment or shopping, products relating to penny auctions or online auctions, products relating to affiliate services, products relating to e-commerce, products relating to sports, media, musical instruments, educational products, financial products, travel & hospitality products, real estate products, sports and sporting events, information on market trends and predictions, mortgage quotes, loans, insurance, advertising, messaging, news feeds, weather, news, real estate products (e.g. vacant land, residential, commercial, recreational, retail, shopping malls, hotels, motels, golf courses, casinos, resorts, marinas, industrial, vacation, time shares, condominiums, multifamily, and other types of real estate, etc.), relocation products, internet marketing, home improvements/remodeling (home warranties, insurance, indoor and outdoor furniture, fixtures, windows, siding, roofing, heating/cooling, solar, plumbing, electrical, mechanical, and similar products), food, grocery, livestock, hair products, resorts, floor coverings, furniture, fixtures and the like.

The term "product provider" as used herein refers to any provider (in any form, e.g., but not limited to a discoverer, inventor, developer, manufacturer, co-developer, marketer, distributor, wholesaler, retailer, importer, exporter, seller, reseller, auctioneer, bidder, agent, representative, and the like of any product.

The term "service" as used herein refers to any service described herein, or as known in the art: non-limiting examples of services include, but are not limited to: search engines or search requests; social, local, mobile search, mobile services, mobile banking and mobile wallet services, entertainment, shopping, penny auctions or online auctions, affiliate services, e-commerce, sports, media and entertainment, educational, personal & financial services, travel & hospitality services, real estate, sports and sporting events, services by service providers, online dating, online gambling, gaming, retail stores, virtual communities, real estate services, advertising, messaging, news feeds, weather, news, real estate services (e.g. leasing, buying or selling of vacant land, residential, commercial, recreational, retail, shopping malls, hotels, motels, golf courses, casinos, resorts, marinas, industrial, vacation, time shares, condominiums, multifamily, and other types of real estate, etc.), brokers, agents, relocation services, internet marketing, concierge, transportation, lenders, appraisers, developers, contractors, inspectors, home improvements/remodeling (home warranties, insurance, roofing, heating/cooling, solar, plumbing, electrical, mechanical, and similar types of services), merchandizing, cleaning, transportation, banking, auctions, estate planning, husbandry, veterinary, medical, cosmetic, spa, moving, relocation, copying, office, management, filing, accountant, beverage services, and the like.

The term "service provider" as used herein refers to any provider (in any form, e.g., but not limited to a discoverer, inventor, developer, manufacturer, co-developer, marketer, distributor, wholesaler, retailer, importer, exporter, seller, reseller, auctioneer, bidder, agent, representative, and the like of any service.

The term "dietary supplement" as used herein refers to a product taken orally that contains an ingredient intended to supplement the diet. "Dietary ingredients" in these products include, but are not limited to vitamins, minerals, herbs or other botanicals, amino acids, and substances such as enzymes, organ tissues, glandulars, and metabolites. Dietary supplements can take the form of extracts and concentrates and can be provided as tablets, capsules, softgels, gelcaps, liquids, or powders. Dietary supplements may also be provided in bars, drinks, shakes and other food products. In general, a dietary supplement is not intended to be the sole item of a meal or diet.

The term "vitamin" as used herein refers to an organic compound required by an organism as a vital nutrient in limited amounts. An organic chemical compound (or related set of compounds) is called a vitamin when it cannot be synthesized in sufficient quantities by an organism, and must be obtained from the diet. Thus, the term is conditional both on the circumstances and on the particular organism. For example, ascorbic acid (vitamin C) is a vitamin for humans, but not for most other animals, and biotin (vitamin H) and vitamin D are required in the human diet only in certain circumstances. By convention, the term vitamin includes neither other essential nutrients, such as dietary minerals, essential fatty acids, or essential amino acids (which are needed in larger amounts than vitamins), nor the large number of other nutrients that promote health but are otherwise required less often. Thirteen vitamins are universally recognized for humans at present: Vitamins A, C, D, E, K, and the B vitamins (thiamine, riboflavin, niacin, pantothenic acid, biotin, vitamin B6, vitamin B12, and folate).

The term "weight loss product' as used herein includes diet pills, shakes, bars, teas, meal replacements; and low-carb items. Foods include beans, fruits, herbs, legumes, natural sweeteners, nuts, oils, seeds, vegetables, acai, bee products, greens, resveratrol and more.

The term "skin care product" as used herein includes bath salts and oils, shampoos, conditioners, lotions, creams, soaps, scrubs, teeth cleaners and whiteners, ointments, elixirs, analgesics, antibiotics, vitamins and minerals.

The term "dietary mineral" as used herein refers to a chemical element required by human body, other than the four elements carbon, hydrogen, nitrogen, and oxygen present in common organic molecules. The term is archaic, as it describes chemical elements rather than actual minerals. The minerals may include calcium, phosphorus, potassium, sulfur, sodium, chlorine, and magnesium. Important "trace" or minor minerals, necessary for mammalian life, include iron, cobalt, copper, zinc, molybdenum, iodine, and selenium.

The term "sports supplements" as used herein refer to dietary supplements commonly used by those involved in bodybuilding and athletics. Sports supplements may be used to replace meals, enhance weight gain, promote weight loss or improve athletic performance. Among the most widely used are vitamin supplements, protein, branched-chain amino acids (BCAA), glutamine, essential fatty acids, meal replacement products, creatine, weight loss products and testosterone boosters. Many sports supplements are also consumed by the general public.

The term "eating regimen" as used herein refers to an eating plan of an individual in terms of calories, carbohydrate intake and protein intake. It may also include the types of food be to eaten and when to eat them. Type of food may include, but not limited to, white meat, red meat, or specific meat such as beef, lamb, different types of vegetables, and sea foods.

The term "personal care product" as used herein refers to consumer products used in personal hygiene or for beautification. Personal care products includes lip balm, cleansing pads, colognes, cotton swabs, cotton pads, deodorant, eye liner, facial tissue, hair clippers, lip gloss, lipstick, lotion, makeup, mouthwash, nail files, pomade, perfumes, razors, shampoo, conditioner, talcum powder, shaving cream, skin cream, toilet paper, wet wipes, toothbrushes, toothpaste and the like.

The term "beauty product" as used herein refers to any product that impacts either one or more conditions of an external body portion of a subject and/or causes of those conditions. Beauty products may include tangible merchandise (cosmetic, non-cosmetic, accessories, or apparel), services (beauty applications, hair styling, hair cutting, hair coloring), diagnostics, beauty regimen (e.g., a combination of merchandise and/or services), and/or advice. Examples of beauty products may include beauty products, such as treatment products, personal cleansing products, and makeup products. Beauty products may be in any form capable of being applied to an external body portion of a subject. Examples of such products include ointments, lotions, creams, gels, oils, sprays, soaps, shampoos, conditioners, scrubs, rinses, washes, etc.

The term "food" as used herein encompasses both natural foods and prepared dishes. Natural foods encompass dairy products, fish, poultry, meat, grains, nuts, seeds, legumes, herbs, spices, vegetables and fruits. Prepared dishes encompass processed foods such as sausage, lunch meat, as well as canned or frozen TV dinners, fast food such as hamburgers, fries, treats such as ice cream, pies, pastries, candies or foods prepared at home.

The term "nutrient" as used herein refers to an element in a food item. It can be a vitamin, mineral, or any subpart present in a food item whether taken in its natural form in natural foods or as a nutritional supplement.

The terms "gaming" or "gambling" as used herein refers to either land-based or online events, activities, games, sessions, rounds, hands, rolls and operations etc., including video games, Web games, online casino, casino games, card games, poker, dice games, online sports betting, sporting events and/or any other gaming or gambling events.

DETAILED DESCRIPTION OF THE PREFERRED EMBODIMENT(S)

For illustrative purposes, the principles of the present invention are described by referencing various exemplary embodiments. Although certain embodiments of the invention are specifically described herein, one of ordinary skill in the art will readily recognize that the same principles are equally applicable to, and can be employed in other systems and methods. Before explaining the disclosed embodiments of the present invention in detail, it is to be understood that the invention is not limited in its application to the details of any particular embodiment shown. Additionally, the terminology used herein is for the purpose of description and not of limitation. Furthermore, although certain methods are described with reference to steps that are presented herein in a certain order, in many instances, these steps may be performed in any order as may be appreciated by one skilled in the art; the novel method is therefore not limited to the particular arrangement of steps disclosed herein.

It must be noted that as used herein and in the appended claims, the singular forms "a", "an", and "the" include plural references unless the context clearly dictates otherwise. Furthermore, the terms "a" (or "an"), "one or more" and "at least one" can be used interchangeably herein. The terms "comprising", "including", "having" and "constructed from" can also be used interchangeably.

In one aspect, the present invention relates to a method of providing assistance to an individual, optionally in real-time, to maintain or improve the individual's wellness, comprising the steps of measuring 100 a presence and/or concentration of one or more biomarkers in a sample from the individual; predicting 200 a wellness need of the individual to maintain or improve the individual's wellness based on the measured presence and/or concentration of the one or more biomarkers where the one or more biomarkers are indicators of the wellness need; and altering 300 the living environment of the individual or providing information, advice, or guidance to the individual for addressing the wellness need of the individual (FIG. 1). The information, advice, or guidance may be given directly to the individual, or to a third party such as an assistant or a caregiver.

In certain embodiments, the present invention may provide real-time assistance to the individual. The assistance is in one of two forms: altering the living environment of the individual and providing information, advice, or guidance to the individual for addressing the wellness need of the individual. In this embodiment, the assistance is given promptly after the sample from the individual is accessed or collected, thus in real-time. Delays from the time the sample is accessed or collected until the assistance is given are minimal. For example, the delays may be on the order of minutes, and possibly a few seconds, but not longer than about one hour. Undue delays caused by the practice such as mailing collected samples to a remote site for biomarker measurement fail to dynamically monitor the biomarkers and provide information, advice, or guidance that addresses in real-time the ever-changing wellness needs of an individual.

Once the sample from the individual is accessed or collected, the biomarkers in the sample are immediately measured to determine their presence and/or concentration. The biomarkers in the sample include polypeptides, polynucleotides (DNA and RNA), metabolites, microbes, inorganic compounds, and ions. The present invention may employ a recognition molecule for measuring a biomarker in the sample, where the recognition molecule can specifically bind to the biomarker. Technologies that utilize a recognition molecule have the advantages of simplicity, low cost and generating measurements within a short period of time. It is well understood by a skilled person in the art that a recognition molecule can be designed and generated after knowing the identity of a biomarker.

In some embodiments, the biomarker in a sample may be correlated to another compound or molecule in the same sample or a different sample. In these embodiments, measuring the correlated compound or molecule may provide advantages in comparison with measuring the biomarker itself. The advantages include easier access to the different sample, more accurate, quick or simple technology available for measuring the correlated compound or molecule. In these embodiments, use of a plurality of biomarkers may provide more accurate prediction of the individual's wellness needs than a single biomarker. In some embodiments, one or more ratios between two biomarkers in the same or different samples may be used to predict the individual's wellness needs. In some embodiments, pattern recognition may be used to evaluate biomarkers where the number of biomarkers is sufficiently large. Also, the correlated compound or molecule may provide an earlier signal for susceptibility of disease or health concerns, thus predicting the wellness needs in earlier stages.

For example, in one embodiment, when a known biomarker is a polypeptide in the sample, the gene encoding such polypeptide can be determined. It is then possible to use a surrogate polynucleotide (such as DNA or RNA) assay to measure the presence and/or concentration of the polypeptide. In this embodiment, the technology for measuring polynucleotide may be simpler or more accurate than available method for measuring the polypeptide directly.

In some embodiments, the biomarker in the sample is a polypeptide. The polypeptide in the sample may be measured by using a recognition molecule selected from an antibody, an antigen, an aptamer, a natural receptor, a synthetic receptor, a ligand, an enzyme, and an enzymatic substrate. The polypeptide can specifically bind to the recognition molecule to form a complex. The complex may be selected from antibody/antigen (antibody/polypeptide when the polypeptide is an antigen, antigen/polypeptide when the polypeptide is an antibody), polypeptide/aptamer, ligand/receptor (polypeptide/natural receptor when the polypeptide is a ligand, polypeptide/synthetic receptor when the polypeptide is a ligand, polypeptide/ligand when the polypeptide is a receptor), enzyme/substrate (polypeptide/enzyme when the polypeptide is a substrate of the enzyme, polypeptide/substrate when the polypeptide is an enzyme).

In some embodiments, the biomarker in the sample is a polynucleotide. The polynucleotide in the sample may be measured by using a recognition molecule selected from an antibody, an aptamer, and a nucleic acid probe that is complementary or matches with the polynucleotide in the sample. The polynucleotide can specifically bind to the recognition molecule to form a complex. The complex may be selected from antibody/polynucleotide, polynucleotide/aptamer, and polynucleotide/nucleic acid probe complexes.

In some embodiments, the polynucleotide in the sample may be amplified before being measured. The amplification method may be PCR, nested-PCR, or RT-PCR.

In some embodiments, the biomarker in the sample is a metabolite. Some common metabolites include amino acids, peptides, nucleosides, nucleotides, and carbohydrates. The metabolite in the sample may be measured by using a recognition molecule selected from an antibody, an aptamer, a natural receptor, a synthetic receptor, and an enzyme. The metabolite can specifically bind to the recognition molecule to form a complex. The complex may be selected from antibody/metabolite, aptamer/metabolite, receptor/metabolite, and enzyme/metabolite complexes.

In some embodiments, the biomarker in the sample is a microbe. The microbe in the sample may include species specific molecules such as polypeptides, polynucleotides, and/or metabolites. Any one of these species specific molecule may be used as an indicator of the presence of the microbe. In some embodiments, the microbe may be lysed to release the content within one or more of the microbial cells for detection of the species specific molecule. Thus, detection of the microbe can be accomplished measuring a species specific molecule including a polypeptide, a polynucleotide, and a metabolite in the lysate. Therefore, the same technologies discussed above for measuring a polypeptide, a polynucleotide, and a metabolite may also be used in detecting certain microbes in the sample from components in a lysate of the sample. The polynucleotide of the microbe may be digested to facilitate the measurement of the polynucleotide.

In some embodiments, the microbe has a species specific cell surface protein, which may be directly measured without lysing the microbe. A recognition molecule for binding the surface protein may be an antibody, an aptamer, a natural receptor, a synthetic receptor or a ligand. The recognition molecule may form a complex with the microbe through binding with the surface protein. The complex may be selected from antibody/microbe, aptamer/microbe, receptor/microbe, ligand/microbe.

Aptamers as a recognition molecule for a specific biomarker (polypeptide, polynucleotide, or metabolite) may be discovered by any method known in the art. In one embodiment, the aptamers are discovered using an in vitro selection process referred to as SELEX (Systematic Evolution of Ligands by Exponential enrichment). See for example Gold et al. (U.S. Pat. Nos. 5,270,163 and 5,475,096), the contents of each of which are hereby incorporated by reference in their entirety. SELEX is an iterative process used to identify a nucleic acid ligand to a chosen molecular target from a large pool of nucleic acids. The process relies on standard molecular biological techniques, using multiple rounds of selection, partitioning, and amplification of nucleic acid ligands to resolve the nucleic acid ligands with the highest affinity for a target molecule. The SELEX method encompasses the identification of high-affinity nucleic acid ligands containing modified nucleotides conferring improved characteristics on the ligand, such as improved in vivo stability or improved delivery characteristics. Examples of such modifications include chemical substitutions at the ribose and/or phosphate and/or base positions. There have been numerous improvements to the basic SELEX method, any of which may be used to discover nucleic acid ligands for use in methods of the invention.

In some embodiments, the recognition molecule of the present invention may be integrated in a biosensor for measuring a biomarker in the sample. The biosensor comprises three main components: a recognition molecule (for example antibodies, antigens, receptors, nucleic acid probes, aptamer or enzymes) that detects the biomarker in the sample; a signal transducer that converts the binding of the biomarker with the recognition molecule into an electronic output; and a signal processor that relays and displays the results (Vo-Dinh et al., "Biosensors and biochips: advances in biological and medical diagnostics," *Fresenius J Anal Chem*, volume 366, pages 540-551, 2000, incorporated by reference herein in its entirety).

The recognition molecule may be fixed on the detection surface of the biosensor by means of physical adsorption, covalent binding, matrix entrapment, inter molecular cross-linking or membrane entrapment. The binding of the biomarker with the recognition molecule is converted to electronic signals by the transducer in the biosensor.

In one embodiment, a plurality of recognition molecules may be integrated in a biosensor for measuring one or more biomarkers in the sample. Such biosensors can separately and independently convert the binding of each biomarker to a separate electronic signal, which indicates the presence and/or concentration of each biomarker in the sample. In this embodiment, a single biosensor is capable of measuring multiple biomarkers in a sample.

In some embodiments, multiple biosensors may be used, each for measuring a separate biomarker in the sample.

According to the mechanism of biomarker detection, there are five types of transducers that may be used in biosensors of the present invention: optical (colorimetric, fluorescent, luminescent, and interferometric) transducers, mass-based (piezoelectric and acoustic wave) transducers, magnetic field based transducers, electrochemical (amperometric, potentiometric and conductometric) transducers, and calorimetric transducers.

Optical transducers may be based on luminescence, fluorescence, colorimetry or interferometry. In particular, selectivity and sensitivity of fluorescence make the fluorescence-based transducers particularly suitable for some embodiments. Fluorescence-based biosensors measure the change in frequency of electromagnetic radiation emission (caused by previous absorption of radiation and the generation of an excited state), and the repeated excitation of recognition molecules produces a bright signal that can be measured even at single-copy of biomarker level.

Optical transducers may use an input grating coupler (e.g., bidiffractive grating coupler), a prism coupler, planar or a nonplanar, polarimetric, ion-exchange or deposited-rib, channelized or non-channelized waveguide or interferometer (e.g. Mach-Zehnder interferometer), as well as surface plasmon resonance sensor (e.g., BIACORE system) using prism coupler, resonant minor with vibro-stirrer (e.g., Iasys), evanescent wave fiber optic biosensor for multi-analyte detection (e.g., RAPTOR antibody identification system), displacement flow detector, or other optical or time-resolved or phase fluorescence transducer (e.g., to detect fluorophore-labeled binding protein or fluorescence resonance energy transfer), or fiber optic elements.

Mass-based transducers include piezoelectric and acoustic wave transducers. Mass-based transducers typically rely on binding the biomarker to a recognition molecule on the surface, whereby the mass of the system increases and this mass increase is detected and/or measured.

Magnetic field-based transducers use a thin-film structure composed of alternating ferromagnetic and non-magnetic conductive layers. The thin-film structure has a quantum mechanical magnetoresistance effect. The surface of the thin-film structure is coated with a recognition molecule. All the molecules (including the biomarker) in the sample are then tagged with a small magnetic (or magnetizable) particle. Upon specific binding of the biomarker on the surface of the thin-film structure and washing away of the unbound molecules, the bound magnetic particles will cause a significant change in the electrical resistance in the thin-film structure. This type of transducer is described in WO 2006/059270 and EP 2 390 651 A1, which are incorporated by reference herein in their entirety.

Electrochemical transducers typically use an enzyme as a recognition molecule, which catalyzes a reaction specific to the biomarker. The reaction causes changes in electrochemical signals. For example, glucose oxidase or lactate oxidase may be immobilized in conducting polymers generated from pyrrole, N-methylpyrrole, aniline and o-phenylenediamine on platinum surfaces. Such biosensor can be used to measure glucose and lactate respectively. In some embodiments, multiple enzymes may be used in a single biosensor for catalyzing a cascade of reactions in order to generate more sensitive and specific electrochemical signals. More details on this type of transducer can be found in US 2011/024309, which is incorporated by reference herein in its entirety.

Calorimetric (or thermometric) transducers measure changes in heat due to exothermic reactions between biomarker and a recognition molecule immobilized on temperature sensitive surface. Changes in temperature can be indirectly used to determine the biomarker concentrations in the sample.

The transducers may be implemented on different physical structures. Examples include a giant magnetoresistance structure (described in WO 2006/059270 and EP 2 390 651 A1); nanowire (described in WO 2012/075445, WO 2007/114649 and EP 1 706 742 A1); microfluidic circuit (described in US 2013/0078620); nanotube (described in WO 2005/088288; WO 2013/033359; and WO 2007/102629), biochip (described in US 2011/0071051). All these references are incorporated by reference herein in their entirety.

Regarding the nanowire or nanotube based transducer, after the biomarker binds to the recognition molecule on the nanotube or nanowire, the binding affects the electrons traveling through the nanowire or nanotube, by changing the conductivity. Therefore, multiple nanowires or nanotubes may be placed in an array on a single transducer for parallel and simultaneous measurement of a plurality of biomarkers.

In one embodiment, the biosensor comprises a semiconducting nanoparticle ion-sensitive field-effect transistor (IS-FET) for detecting immunoglobulin G (IgG) in a modified conventional enzyme-linked immunosorbent assay (ELISA). Indium oxide and silica nanoparticles are layer-by-layer self-assembled with the oppositely charged polyelectrolyte as the electrochemical transducer and antibody immobilization site, respectively. The indium oxide nanoparticle ISFETs generate electric signals in response to the concentration of target IgG. The sandwiched ELISA structure catalyzes the conversion of the acidic substrate into neutral substance with the aid of horseradish peroxidase. The pH change in the sample solution is detected by nanoparticle ISFETs. See Lee et al., "An electric detection of immunoglobulin G in the enzyme-linked immunosorbent assay using an indium oxide nanoparticle ion-sensitive field-effect transistor," *J. Micromech. Microeng.*, volume 22, page 015009, 2012, which is hereby incorporated herein by reference in its entirety.

In some embodiments, the recognition molecules in the biosensor may be reused. More specifically, after a measurement, the biomarker bound to the recognition molecules may be removed from the biosensor. Thus, the recognition molecule may be used again for another measurement of the biomarker at a later time. The removal of the bound biomarker may be accomplished by using a washing buffer, changing pH, temperature, and/or ionic strength of a solution. Any procedure known to a person skilled in the art that can remove the bound biomarker without causing an irreversible change or damage to the recognition molecules may be used for the present invention. The procedure for removing the bound biomarker is highly dependent on the identity of the recognition molecule. For example, if the recognition molecule is a nucleic acid probe, the complex of nucleic acid probe/biomarker may be dissociated by raising the temperature above the denaturing temperature of the complex to disassociate the complex and the biomarker may then be washed sway.

In some embodiments, the recognition molecule is a conditionally active antibody that specifically binds to the biomarker. Conditionally active antibodies and methods of generating them are described in, for example, US 2012/0258865, US 2012/0164127, and US 2010/0260739. The conditionally active antibody may be reversibly inactivated at a condition (temperature, pH, osmotic pressure, osmolality, oxidation and electrolyte concentration), thus releasing the bound biomarker. The conditionally active antibody will return to an active state after the condition is removed for the next measurement. For example, the conditionally active antibody may be inactivated at high temperature and will thereby release the bound biomarker. The released biomarker may be washed away. Once the temperature is reduced, the conditionally active antibody becomes active again and ready for the next measurement. In another embodiment, the conditionally active antibody may be inactivated at high pH and releasing the bound biomarker. Once the pH is reduced, the conditionally active antibody becomes active again and ready for the next measurement.

In some embodiments, the biomarker in the sample is an inorganic compound or an ion. The inorganic compounds in the sample may include oxygen, nitrogen oxide, and hydrogen, in a sample (such breath or dissolved in a bodily fluid). The ions include $H^+$, $K^+$, $Na^+$, $Mg^{2+}$, $Ca^{2+}$, $Mg^{2+}$, $Cl^-$, $HCO_3^-$, $PO_4^{3-}$, $NH^4$, and $OH^-$ in the sample. Examples of a suitable assay for measuring the inorganic compound or ion are described in Wan et al. "Determination of major inorganic ions in blood serum and urine by capillary electrophoresis with contactless conductivity detection," *Analytica Chimica Acta*, volume 525, pages 11-16, 2004; US 2003/0045827; and Xia et al., "Colorimetric detection of DNA, small molecules, proteins, and ions using unmodified gold nanoparticles and conjugated polyelectrolytes," *PNAS*, vol. 107, pages 10837-10841, 2010, which are incorporated herein by references in their entirety.

In some embodiments, the present invention uses an electrode to measure the inorganic compound or ion in the sample. One type of electrode is an electrochemical electrode that measures an electrochemical signal produced during a chemical interaction between an inorganic compound or ion and a substrate on which electrochemical molecules are bound or consumed. Such electrodes can be categorized into potentiometric, amperometric and conductometric electrodes depending on the electrochemical signals they measure.

Electrochemical electrodes for gaseous biomarkers (such as these in breath or fart gas) operate by reacting with the gaseous biomarker and producing an electrical signal proportional to the gaseous biomarker concentration. Such electrodes typically consist of a sensing electrode (or working electrode), and a counter electrode separated by a thin layer of electrolyte. The gaseous biomarker reached the sensing electrode will react at the surface of the sensing electrode through either an oxidation or reduction mechanism. These reactions are catalyzed by the electrochemical materials specifically developed for the catalyzing reaction of the gaseous biomarker.

Any suitable electrochemical electrodes may be used to measure an inorganic compound in the sample. For example, there are electrochemical electrodes known for measuring $NH_3$, $Br_2$, CO, $Cl_2$, $ClO_2$, $B_2H_6$, $F_2$, $GeH_4$, $H_2$, HCl, HCN, HF, $H_2S$, NO, $NO_2$, $O_2$, $O_3$, $PH_3$, $SiH_4$, $SO_2$. Some examples of electrochemical reactions include the follows:

$$CO+H_2O \rightarrow CO_2+2H^++2e^-$$

$$H_2S+4H_2O \rightarrow H_2SO_4+8H^++8e^-$$

$$NO+2H_2O \rightarrow HNO3+3H^++3e^-$$

$$H_2 \rightarrow 2H^++2e^-$$

$$2HCN+Au \rightarrow HAu(CN)_2+H^++e^-$$

Besides the biosensors and electrochemical electrodes discussed above, there are other technologies that may also be used in the present invention to measure the biomarkers in the sample.

Magnetic bead tagged recognition molecules may provide a fast and efficient technology of measuring biomarkers at low cost. The magnetic beads preferably have a hydrophilic surface to reduce non-specific binding. The magnetic beads are coated with a recognition molecule, which specifically binds to a biomarker. The magnetic beads are then separated from the sample by magnetic separation (using a magnet). Magnetic beads have high surface areas per unit volume, good stability, and enable fast kinetic processes involving samples in solution. The biomarker bound to the magnetic beads may be detected in a selective way, either by using different labels for different proteins in a bar-code like approach, or by first sorting beads with the same recognition molecule based on the proteins they have captured, then detecting recognition molecules on each type of magnetic bead. See Mani et al. "Magnetic particles in ultrasensitive biomarker protein measurements for cancer detection and monitoring," *Expert Opin Med Diagn.*, volume 5, pages 381-391, 2011 for more details, which is incorporated herein by reference in its entirety.

Nanoparticles may also be used to tag the recognition molecule (see Geho et al., 'Nanoparticles: potential biomarker harvesters," *Curr Opin Chem Biol.*, volume 10, pages 56-61, 2006, incorporated herein by reference). Nanoparticles that exhibit unique physical properties, such as particle aggregation and photoemission, and electrical and heat conductivities and/or chemical properties, such as catalytic activity, may be used to detect biomarkers in the sample. For example, when the biomarker is a polynucleotide, a nanoparticle tagged recognition molecule (e.g. a nucleic acid probe) can form a complex with the polynucleotide biomarker, which can produce a significantly sharper decrease in the slope of melting curves because of the specific aggregation property of the nanoparticles. Thus, a much higher sensitivity may be achieved as compared with using untagged nucleic acid probe. In some other embodiments, the wavelength of emitted light from nanoparticles may shift after binding of a biomarker to the recognition molecule on the nanoparticle. Aggregation of nanoparticles also causes emission light shifts. See Liu, "Nanoparticles and their biological and environmental applications," *Journal of Bioscience and Bioengineering*, volume 102, pages 1-7, 2006, which is incorporated herein by reference in its entirety. The emission light shift can be used as an indication of the presence of the biomarker.

Quantum dots may also be used to measure biomarkers in the sample. Quantum dots offer several advantages, such as size- and composition-tunable emission from visible to infrared wavelengths, large absorption coefficients across a wide spectral range, and very high levels of brightness and photostability. In particular, quantum dots can be used to quantify a panel of biomarkers in the sample, since a single quantum dot is large enough for conjugation to multiple recognition molecules, leading to enhanced binding affinity and specificity through a "multivalency" effect. These features are especially useful for the measurement of biomarkers that are present at low concentrations in the sample. In embodiments where multiple biomarkers are used, the recognition molecules for each biomarker may be conjugated on a single quantum dot. Thus binding of the different biomarkers may cause simultaneous excitation resulting in a multiple wavelength quantum dot emission. See Xing et al., "Quantum dot bioconjugates for in vitro diagnostics & in vivo imaging," *Cancer Biomarkers*, volume 4, pages 307-319, 2008, which is incorporated herein by reference in its entirety.

When the recognition molecule is an antibody, technologies such as protein immunostaining, protein immunoprecipitation, immunoelectrophoresis, immunoblotting, and Western blot may be used for the present invention. When the recognition molecule is a natural receptor, a synthetic receptor, a ligand, a nucleic acid probe or an aptamer, technologies that may be used for detecting the target may be selected from spectroscopic methods (such as UV spectrophotometry, fluorescence, circular dichroism), calorimetry, chromatographic methods, filter-based methods, gel mobility shift assays, ligand competition assays.

In some embodiments, spectroscopy based methods may be used to measure the biomarker. Often the ligand and/or receptor interact with electromagnetic radiation (such as light) so that they either perturb the radiation in a measurable manner or respond to the input radiation by emitting their own characteristic signals. One example of spectroscopic methods is ultraviolet spectrophotometry. If a range of wavelengths is scanned for emission, the plot of intensity vs. emission wavelength is known as an emission spectrum. Alternately, it is possible to vary the wavelength of the excitation light and measure intensity at a single emission wavelength. Another example is circular dichroism, which uses polarized light of a particular wavelength passes through solution followed by detection the difference in absorbencies of the right and left-handed light (the ellipticity, θ). The ellipticity is plotted as a function of wavelength.

For each type of spectroscopy, the general idea is that the free biomarker (a free ligand and/or free receptor) has a characteristic "signal" or "signature." However, when a complex (ligand+receptor) is formed with the recognition molecule, the spectroscopic properties of the molecule(s) as part of the complex may be very different than when the biomarker is unbound. In such cases, the changes in spectroscopic signals can be used to determine the relative concentrations of free and bound biomarkers.

In some embodiments, calorimetry may be used to measure the biomarker in the sample. When a ligand binds to a receptor, heat may be generated (or absorbed). In calorimetry, a receptor is titrated with a ligand in a calorimeter and heat production is measured at each point in the titration. The heat generated is proportional to the amount of one or more complexes formed in the solution.

In some embodiments, chromatographic binding methods may be used to measure the biomarker in the sample. One type of chromatographic binding method is affinity chromatography. In this method a column is used with a chromatography column resin coated with a tightly bound recognition molecule. A solution of the biomarker is applied to the column so that the biomarker will bind to the recognition molecule on the resin. Then, elution is carried out by applying a low to high concentration gradient of a second molecule, whose affinity for the recognition molecule is known. The concentration at which the second molecule displaces the biomarker from the column is directly related to the dissociation constant.

In some embodiments, filter-based binding assays may be used to detect the biomarker in the sample. These methods are commonly used in pharmacology to detect binding of radioisotopically labeled biomarker to a recognition molecule on a membrane. The membranes containing the recognition molecule are mixed with the biomarker. The mixture is then filtered so that the membrane containing the recognition molecule and bound biomarker remain in the filter. The filter is then washed to remove any residual unbound substance and then subjected to scintillation counting to detect and quantitate the amount of bound biomarker.

In some embodiments, gel mobility-shift binding assays may be used to measure the biomarker in the sample. In polyacrylamide gel electrophoresis a polymer matrix is used, which is a network of interconnected pores of fairly uniform size. Biomarkers and recognition molecules may independently travel through the matrix driven by an electric field. The complex of biomarker/recognition molecule, being larger than each of the biomarker and recognition molecule, travels much slower in the same matrix. Thus, after running the gel, the exact amount of biomarker in the sample (and sometimes the concentrations of the complexes) can be determined by autoradiography, densitometry, or scintillation counting.

A protein microarray may also be used to detect multiple biomarkers in the sample. The microarray does not require pre-separation of the polypeptides in the sample. A protein microarray consists of a support surface such as a glass slide, nitrocellulose membrane, bead, or microtitre plate, to which an array of capture proteins is bound. The capture proteins, typically antibodies, bind to the biomarkers in the sample. The biomarkers bound to the antibodies on the microarray are then detected using a laser scanner. Protein microarrays are rapid, automated, economical, and highly sensitive. More details on protein microarray are described in U.S. Pat. Nos. 4,591,570; 4,829,010; and 5,100,777, which are incorporated herein by reference in their entirety.

In some other embodiments, the aptamers may be fixed on an array for detecting multiple biomarkers in the sample. Each aptamer is fixed at a microscopic spot on the surface of the array. The binding of a biomarker to its specific aptamer on the array may be detected by direct fluorescence detection of fluorescent reporters, fluorescence anisotropy, fluorescence resonance energy transfer (FRET), surface plasmon resonance (SPR) imaging, and electrochemical detection. See Baldrich, "Aptamer array", *Methods Mol. Biol.*, volume 671, pages 35-54, 2011, which is incorporated by reference in its entirety.

In some embodiments, oligonucleotide probes are fixed on at a microscopic spot on a solid surface. Thus, tens of thousands of probes may be fixed on a single chip, which enables parallel detection of up to thousands of polynucleotides in a sample. The DNA microarray may be custom built to specifically detect certain species of polynucleotides (biomarkers) in a sample. In some embodiments, commercial DNA microarrays may be used for detecting as many polynucleotides as possible in a sample. Commercial DNA microarrays include these made by Affymetrix "Gene Chip", Illumina "Bead Chip", Agilent single-channel arrays, the Applied Microarrays "CodeLink" arrays, and the Eppendorf "DualChip & Silverquant." More details on the DNA microarray technology may be found in Shalon D, Smith S J, Brown P O (1996). "A DNA microarray system for analyzing complex DNA samples using two-color fluorescent probe hybridization". *Genome Res* 6 (7): 639-645; Yuk Fai Leung and Duccio Cavalieri, Fundamentals of cDNA microarray data analysis. TRENDS in Genetics Vol. 19 No. 11 Nov. 2003; Schena M, Shalon D, Davis R W, Brown P O (1995). "Quantitative monitoring of gene expression patterns with a complementary DNA microarray". *Science* 270 (5235): 467-470; and Pease et. al, "Light-generated oligonucleotide arrays for rapid DNA sequence analysis". *PNAS* 91 (11): 5022-5026 (1994), which are incorporated herein by reference in their entirety.

In some embodiments, an ion torrent sequencing based method may be to measure the biomarker in the sample when the biomarker is a polynucleotide. See Pennisi, "Semiconductors inspire new sequencing technologies," *Science* volume 327, page 1190, 2010 and Perkel, "Making contact with sequencing's fourth generation". *Biotechniques,* 2011, incorporated herein by reference in their entirety.

In some embodiments, ion torrent sequencing may be used to measure the biomarker in the sample when the biomarker is a polynucleotide. See Pennisi, "Semiconductors inspire new sequencing technologies," *Science* volume 327, page 1190, 2010 and Perkel, "Making contact with sequencing's fourth generation". *Biotechniques,* 2011, which are hereby incorporated herein by reference in their entirety.

The measurement of biomarkers in the sample may be, for example, a passive, recurring measurement, rather than an active measurement. Passive measurements are measurements which do not require an operator or initiation but rather can be programmed to occur automatically on a time schedule or responsive to a particular activity or event. In some embodiments, a bodily fluid may be periodically, or at any preset schedule, analyzed to measure the biomarkers within. These measurements may be longitudinal measurements where the past measurements are used to establish a baseline for a particular biomarker.

In some embodiments, the present invention may also collect map location data on where the biological phenotype data is measured. This may be based on a mobile device that has an installed map service such as Google maps, Yahoo maps, and Mapquest. In addition, this mobile device may also have a function of monitoring environmental factors at the location where the biological phenotype data is measured. These environmental factors may include weather (temperature, humidity, sunny/raining), UV light intensity, pollen count, etc.

In some embodiments, data from the location (map) is correlated with time at the location and any orthogonal data from the location such as, but not limited to, temperature, altitude noise, altitude, wind, humidity, pollution, oxygen, sunshine, pollen, crowd density, concrete, grass, night, day, near highway and traffic density at that time, aircraft flying, cosmic radiation levels, radon exposure, clothing and physiological conditions. Thus, in these embodiments, other data is collected and saved in addition to measurement of one or more biomarkers so that such other data can be correlated with or used on conjunction with the biomarker data to predict one or more wellness needs.

Based on the measurements of the one or more biomarkers in the sample from the individual, the present invention predicts 200 a wellness need of the individual for maintaining or improving the individual's wellness. The one or more biomarkers may indicate risk factors for certain health concerns or even diseases. The health concerns and diseases include physical or mental diseases and disorders. Furthermore, there is a large body of knowledge of wellness needs for an individual who is at risk of, susceptible to, or has contracted a disease or has a health concern.

The use of biomarkers as indications of risk factors for disease or health concerns is well-documented. Many databases are available with large collections of biomarkers for diseases. Examples include BiomarkerDigger (available at http://biomarkerdigger.org), biomarker databases (available at http://www.liatrisbio.com/biomarker_databases.html), diagnostic and prognostic biomarker database (available at http://www.sciclips.com/sciclips/diagnostic-biomarker-prognostic-biomarker-db.do), BiomarkerBase (available at http://www.biomarkerbase.com/), Biomarker Database (available at http://cancer.jpl.nasa.gov/documents/applications/biomarker-database), and the GVK Biosciences Clinical Biomarker Database (available at https://gobiomdb.com/gobiom/).

Some biomarkers are also described in U.S. provisional application No. 61/895,964, entitled "PHENOTYPIC INTEGRATED SOCIAL SEARCH DATABASE AND METHOD," filed on even date herewith, the entire disclosure of which is incorporated herein by reference. Further, some illustrative examples of the use of biomarkers are given below.

Jagannath et al. found that the presence of certain proteins in the CRTC1-SIK1 pathway may change a mammal's reaction to natural light, i.e. altering circadian system functions ("The CRTC1-SIK1 Pathway Regulates Entrainment of the Circadian Clock," Cell, volume 154, pages 1100-1111, 2013). The authors analyzed the transcriptome of relevant cells in responding to light-regulation and identified a key role for salt inducible kinase 1 (SIK1) and CREB-regulated transcription coactivator 1 (CRTC1) in clock re-setting.

There are studies suggesting that metabolites in a bodily fluid of an individual are correlated with human behaviors. For example, Kandel et al. ("Urine nicotine metabolites and smoking behavior in a multiracial/multiethnic national sample of young adults," *Am J Epidemiol*, volume 165, pages 901-910, 2007) discovered that the urine metabolites generated from nicotine metabolism are correlated with human smoking behavior. Specifically, the ratio of trans-3'-hydroxycotinine to cotinine is correlated with multiple measures of smoking behavior and nicotine dependence in a large.

Another example is from Traskman et al. ("Monoamine metabolites in CSF and suicidal behavior," *Arch Gen Psychiatry*, volume 38, pages 631-636, 1981) which discovered several monoamine metabolites in the cerebrospinal fluid that are correlated with suicidal behaviors. These metabolites include 5-hydroxyindoleacetic acid (5-HIAA), homovanillic acid (HVA), and 3-methoxy-4-hydroxyphenyl glycol (MHPG). The humans made suicide attempts have a significantly lower 5-HIAA level than the controls, especially those who had made more violent attempts. Concentrations of 5-HIAA also were lower than normal in suicidal patients who were not diagnosed as depressed at the time of lumbar puncture, while HVA levels were lowered only in the depressives. A similar observation was also made in urine (Ostroff et al. "The norepinephrine-to-epinephrine ratio in patients with a history of suicide attempts," *Am J Psychiatry*, volume 142, pages 224-227, 1985), where three depressed patients who had made serious suicide attempts had a significantly lower 24 hour urine norepinephrine to epinephrine (EPI) ratio than 19 depressed patients who had made no suicide attempts.

Some bacteria in humans have been found to alter human behavior. In a scientific news article ("Gut feelings: the future of psychiatry may be inside your stomach," available at http://www.theverge.com/2013/8/12/4595712/gut-feelings-the-future-of-psychiatry-may-be-inside-your-stomach, accessed on Aug. 30, 2012), it was disclosed that multiple studies found that alteration of the bacteria population in guts of mice will significantly change the behavior of the mice. In addition, the news article also discussed that doctors have been using probiotics to change the microbial populations in human guts in order to manage obsessive-compulsive disorder and Attention Deficit Hyperactivity Disorder (ADHD). Probiotics are known to add bacteria to or balance the microbial population (microflora) in human guts.

Gut bacteria in humans have also been found capable of affecting the tendency towards obesity (Greenfieldborce, "Fat Bacteria in Human Guts Tied to Obesity," available at http://www.npr.org/templates/story/story.php?storyId=6654607, accessed Sep. 8, 2013). It was disclosed that obese mice have significantly different bacteria in their guts, in comparison with skinny mice. The microbes in human guts will get into stool and therefore may be easily detected. The number of microbial species in human guts is very large. By one estimate, there may be over 320,000 viruses in mammals (see "First estimate of total virus in mammals," available at http://phys.org/print297403030.html, accessed on Sep. 3, 2013).

Other examples include that AMPK (AMP-Activated Protein Kinase) is normally expressed during exercise; glucose is associated with higher energy or weak feelings depending on whether moderately high or low levels are present; catecholamines (adrenalin) in urine are linked to stress; epinephrine is associated with focus and fight-or-flight response; dopamine is associated with pleasure and higher levels observed in extroverts; and IL6 is associated with stress and depression. Dimethylsulfone in breath is associated with skin cancer; acetone level in breath is associated with diabetes; and ammonia compounds in breath may signal liver and kidney disease.

Regarding the wellness needs for an individual who is at risk of, susceptible to, or has contracted a disease or has a health concern, there are several well-known resources that document human diseases and health concerns, as well as information on wellness needs for these diseases and health concerns, such as activities and dietary practices for preventing or reducing the severity of the disease (disease control or even treatment). Examples of such resources are the "Medical Encyclopedia" maintained by the National Institute of Medicine (http://www.nlm.nih.gov/medlineplus/encyclopedia.html) and MedlinePlus (http://www.nlm.nih.gov/medlineplus/).

For example, the entry for Asthma in the Medical Encyclopedia states that many daily life factors may lead to asthma, such as animals (pet hair or dander), dust, chemicals in the air or in food; exercise, mold, pollen, respiratory infections, strong emotions (stress), and tobacco smoke. Thus, wellness needs for an individual that is at risk of asthma may include reducing exposure to these daily life factors. In addition, the entry also lists activities to prevent asthma or reduce asthma attacks, including, for example:

Cover bedding with "allergy-proof" casings to reduce exposure to dust mites.
Remove carpets from bedrooms and vacuum regularly.
Use only unscented detergents and cleaning materials in the home.

Keep humidity levels low and fix leaks to reduce the growth of organisms such as mold.

Keep the house clean and keep food in containers and out of bedrooms—this helps reduce the possibility of cockroaches, which can trigger asthma attacks in some people.

If a person is allergic to an animal that cannot be removed from the home, the animal should be kept out of the bedroom. Place filtering material over the heating outlets to trap animal dander.

Eliminate tobacco smoke from the home. This is the single most important thing a family can do to help a child with asthma. Smoking outside the house is not enough. Family members and visitors who smoke outside carry smoke residue inside on their clothes and hair—this can trigger asthma symptoms Thus, if a sample from an individual has one or more biomarkers for asthma, one or more of the above daily life factors and activities can be implicated as wellness needs for the individual, since avoiding the risk factors and conducting the positive activities are beneficial to maintain or improve the wellness of the individual.

Another disease resource is the "Disease and Conditions" collection maintained by Mayo Clinic available at http://www.mayoclinic.com/health/DiseasesIndex/DiseasesIndex. For example, the entry for depression indicates several activities a person may do to prevent or reduce severity of depression, such as simplifying the person's life, cutting back on obligations, setting reasonable goals, writing in a journal to expressing pain, anger, fear or other emotions, joining a support group and avoiding isolation, participating more in social activities, eating a healthy diet, exercising regularly, getting plenty of sleep, practicing meditation, yoga or tai chi, structuring daily activities by making a list of daily tasks and using a planner to stay organized. Some other activities may also help a person to reduce or prevent depression such as increasing resilience and boosting low self-esteem. Thus, if a sample from an individual has one or more biomarkers for depression, these items may be indicated as wellness needs for the individual.

The above resources are examples for illustrating how detection of the presence and/or concentration of biomarkers for a disease or health concern may be used to predict a wellness need of the individual for maintaining or improving the individual's wellness. Other resources besides the ones maintained by the National Institute of Medicine and the Mayo Clinic may also be used to provide information on wellness needs for an individual at risk of disease or a health concern.

In some embodiments, all of the information on biomarkers and wellness needs of diseases or health concerns may be stored in a database 14. The database 14 is capable of providing a link between one or more biomarkers and a disease or health concern, with the latter further linked to a wellness need. The database 14 includes a large collection of correlations between biomarkers and diseases or health concerns, as well as a collection of wellness needs associated with such diseases or health concerns.

In some embodiments, the present invention may use a phenotype of an individual, together with the biomarkers of an individual, to predict the wellness needs of the individual The physiological phenotype may include, for example, the following physiological parameters:

Physical—motion such as eye movements, anthropometrics (e.g. waist, height, weight measurements), tissue structure and composition.

Metabolic—vital signs (heart rate, blood pressure, respiration rate, temperature), basal metabolic rate, hydration status.

Cardiovascular/Pulmonary—heart functionality (ECG, heart rate variability), respiratory rate/volume, arterial resistance/stiffening, arterial blockage, venous return, peripheral circulation, microcapillary proliferation/circulation.

Organs—size, composition and functionality, (e.g. kidney functionality, liver functionality, adipose tissue disposition, skin thickness/plasticity), pupil dilation, galvanic response.

Muscular/Skeletal—electromuscular activity (e.g. latent or stimulated), strength, composition, oxygenation, density.

Gastro-Intestinal—digestive activity and efficiency.

Thus, in these embodiments, the physiological parameters of the individual may provide supplemental information to the biomarkers in the sample for prediction of the individual's wellness needs.

In some embodiments, data from the location (map) is correlated with time at the location and any orthogonal data from the location such as, but not limited to, temperature, altitude noise, altitude, wind, humidity, pollution, oxygen, sunshine, pollen, crowd density, concrete, grass, night, day, near highway and traffic density at that time, aircraft flying, cosmic radiation levels, radon exposure and clothing. Thus, in these embodiments, other data is collected and saved in addition to measurement of one or more biomarkers and/or physiological parameters so that such other data can be correlated with or used in conjunction with the biomarker data and/or physiological parameters to predict one or more of the individual's wellness needs.

Based on the predicted wellness needs of the individual, the present invention provides assistances to the individual for maintaining an enhanced level of wellness or improving the wellness of the individual. The present invention contemplates that, based on a predicted wellness needs, there are many ways to assist the individual. Such assistance may be divided into two categories: altering 300 the living environment of the individual and providing information, advice, or guidance to the individual.

Altering the individual's living environment may include adjusting brightness and/or color of lighting, changing lighting such as from a fluorescent bulb to a candle, adjusting room temperature, adjusting humidity, rearranging furniture, playing certain music or adjusting the volume of music, changing a TV channel or adjusting a TV sound volume, playing a recorded voice or sound (such as sound of ocean, wind, birds, bugs, recorded messages, sermons), projecting pictures on wall/screen, retracting a roof, opening or closing windows and/or doors, adjusting oxygen concentration in the air, adding or adjusting a scent in the air, introducing one or more air-borne chemicals such as air freshener, oxygen, stimulants, anti-depressants, a mental and/or emotional stress suppressor and/or a mood improver, recommending menus, automatically designing a grocery list and having it automatically delivered, changing hot tub, pool or floor temperature, adjusting humidity, adjust massage strength on massaging devices, evaluating allergic response to pets, personalizing environmental changes, for example adjusting environment of a single room for house guests or pets, and the like.

For example, elevated C-reactive protein in blood is a risk factor or correlated with depression. When an individual's blood is analyzed and find the protein level is elevated in the blood, then a signal may be sent, to adjust the brightness and color of lighting in the room, play happy music to cheer up the individual or to take one or more other actions to alter the living environment of the individual.

In yet other embodiments, the prediction of wellness needs may be used for altering web search results, such as Google®, Bing® search results or some type of display on a user device. For example, the display may be altered such that items that may address the person's wellness needs may be displayed prominently.

Providing information, advice, or guidance to the individual comprises communicating information, advice, or guidance to the individual that may help the individual to perform certain acts in order to address the individual's wellness needs. The specific information, advice, or guidance may be a course of action for the individual to carry out. The course of action may be a plan for the individual to maintain or improve the individual's wellness by directly addressing or satisfying one or more wellness needs.

Some examples of an advised course of action may include, seeking professional counseling, traveling, exercising (hiking, jogging, biking, playing tennis, playing basketball, playing hockey, canoeing, swimming), relaxing (taking deep breath, fast walking, stretching), meeting with a friend, an eating regimen (diet schedule, a particular meal menu, type of foods), drinking wine or another beverage, watching a movie, playing a video game, shopping or a suggestion to visit a particular type of store, dining or a suggestion for a particular type of restaurant, visiting a beach, wearing a particular type of outfit or clothing, wearing a type of hairstyle, talking to a friend, using a dating service, recommending to advertisers which individuals or businesses might be receptive, recommending to people which advertisers or service providers are best to listen to, evaluating wines, food, and nutrients that are more compatible or preferred, determining which television or computer screen is more compatible, and the like. Further, information may be applied for self-directed research and provides a system for easy interpretation and rapid communication to a wireless device such as a smart phone, computer, television, or for printout.

In one exemplary embodiment, biomarkers of asthma are used by the present invention to assist an individual to maintain or improve wellness in terms of preventing asthma or reducing the severity of asthma. There are early inflammatory biomarkers in the breath indicative of the potential for asthma. In particular, exhaled breath condensation may contain inflammatory biomarkers such as cytokines, chemokines and adhesion molecules. These inflammatory biomarkers are early signs of asthma. See van de Kant et al., "Early diagnosis of asthma in young children by using non-invasive biomarkers of airway inflammation and early lung function measurements: study protocol of a case-control study," *BMC Public Health*, volume 9, page 210, 2009, as well as Corradi et al., "Exhaled breath biomarkers in asthmatic children," *Inflamm Allergy Drug Targets*, volume 6, pages 150-159, 2007. Alternative or additionally, other asthma biomarkers in the breath include carbonyl sulfide, hydrogen peroxide, nitric oxide and carbon monoxide. These biomarkers can also be used in predicting wellness needs for an individual.

Early diagnosis of asthma or determination that an individual may develop asthma can provide the opportunity for an individual to effectively manage or prevent asthma-like symptoms, improving wellness of the individual. Some possible courses of action the present invention may provide to individual with these asthma biomarkers may include: avoiding pets or suggesting animal breeds that do not shed hair; steps for keeping dust in the air or in the house at a minimal level; eating food with less chemicals; staying away from mold and pollen; not smoking tobacco; taking immediate measures when a respiratory infection is contracted; and avoiding strong emotions. Such information, advice, or guidance may be conveyed to the individual if the asthma biomarkers are detected in exhaled breath condensation of the individual in order to address one or more of the individual's wellness needs.

In one embodiment, the information, advice, or guidance to an individual at risk of asthma for maintaining wellness may be a travel guide and recommendations for places with mild weather and clear air. The travel guide may also include recommendations for one or more suitable outdoor activities.

In another embodiment, the present invention may alter the living environment of the individual with the asthma by cleaning the air in the room or entire house, such as by activation of one or more air purifiers, initiating an air ventilation system, cleaning an air ventilation system or changing a filter.

In another exemplary embodiment, biomarkers for depression are used by the present invention to assist an individual in maintaining or improving wellness in terms of preventing episodes of depression or reducing symptoms of depression. In a news article titled "Scientist closer to finding tests for depression biomarkers," Yan discussed several biomarkers in blood that may provide early signals for developing depression: elevated C-reactive protein, tumor necrosis factor and interleukin-1beta. See *Psychiatric News*, volume 48, pages 23-27, 2013. Early diagnosis of depression or determination that an individual may develop depression can provide the opportunity for an individual to effectively manage or prevent onset of depression thereby improving the wellness of the individual.

Some possible courses of action that the present invention may provide to such an individual with one or more detected depression biomarkers include simplifying the individual's life, cutting back on obligations and setting reasonable goals, writing in a journal to express pain, anger, fear or other emotions, joining a support group and avoiding isolation, participating more in social activities, eating a healthy diet, exercising regularly, getting plenty of sleep, practicing meditation, yoga or tai chi, and structuring daily activities by making a list of daily tasks and using a planner to stay organized. Some other activities that may also help a person avoid depression include increasing resilience and boosting low self-esteem. Thus, if a sample from an individual has one or more biomarkers for depression, these activities (as wellness needs) will help the individual to improve wellness.

In yet another exemplary embodiment, the length of the telomere of human chromosome may be a biomarker for lifespan. A longer telomere indicates that an individual has a longer life expectancy. The detection of telomere shortening may lead to prediction of wellness need such taking anti-oxidants (e.g. Coenzyme Q-10, Vitamin C), exercising regularly, eating foods rich in antioxidants such as colorful vegetables and fruits like berries, beets, and tomatoes, eating a low-salt, low-fat diet with plenty of fruits, vegetables, and fiber, not smoking, drinking moderately (such as no more than two drinks a day for men, one drink per day for women). These activities are known aging management exercises.

The specific information, advice, or guidance may also be a suggestion for a product or a service for the individual. Such product or service are these wanted, needed or suitable for people with the wellness needs. The product or services are not limited to any particular categories. Some illustrative examples of products include dietary supplements (minerals, vitamins), vitamins, wine, beauty products, personal care products, weight loss products, skin care products, sports supplements, extracts, probiotics, seasonings, flavors, sweeteners, taste/aroma blockers/modifiers, bulking agents, video games (online or using game consoles), electronics (such as cellular smart-phones, wireless organizers, notebook computers, tablet computers, electronic game device, digital photograph album, digital camera), beverages (coffee, tea, juice, soda), books or magazine, music, movies (theater, movies on DVD, movies on Blu-Ray, online stream movies), TV programs, live shows, apparel, home appliances, exercise equipment, types of food, boats, automobiles, bikes, office supplies, furniture, and vacation resorts/destinations.

In one embodiment, the individual may be predicted to be in an early, pre-depression state. The present invention may suggest to the individual a product such as a happy movie, some beauty products, a nice restaurant, video games, or a gift.

Some examples of services that may be suggested by the present invention include messaging services, financial services, dating services, catering services, home cleaning services, home improvement services, hair dressing services, cosmetic services, professional counseling services, travel services, casino gaming services, shopping services, real estate services, sports services, entertainment services, online auction services, hospitality services, department stores, car dealers, travel agents, hotels, spas, insurance companies, providers of heating and cooling systems, mattress stores.

The information, advice, or guidance provided by the present invention may also include promotions, online promotions, coupons, or online coupons for one or more of the suggested products/services. A promotion may include any type of information in any language or translated into any language or scripting social media content in any language or translated into any language relating to any product or service for the purpose of promoting that product or service, and includes, but is not limited to, any type of advertisement, advertising, ad, marketing, coupon, discount, offer, daily deal, auction, and the like.

Promotions for the product/service may be distributed via a media selected from social media advertising, text ad, tweet ad, online marketplace ad, online marketplace video, online auction ad, share ad, online print media ad, telecommunication ad, online coupons, position-based services, ad links, location-based services, location-based promotions, location-based offers, location-based coupons, promotions or offers in connection with an online or mobile news feed, location-based discounts or daily deal ads, location-based advertising, location-based ads, location-based marketing, location-based commerce, mobile ads, mobile ad network, mobile advertising, mobile commerce, mobile location-based advertising and promotions or offers, mobile banking and mobile wallet services, customer loyalty cards, discounts and promotions or offers and online or mobile payment systems for coupons, promotions, offers, and coupons, promotions or offers in connection with an online or mobile news feed or offer and online or mobile coupons and promotions or offers for products and/or services, discount ad, social media web or similar types of position-based services, discount ad, merchant ad, email coupon, merchant ads, video clip ads, video upload or presentations site ads or links, gambling ad, gambling site, sports or sports related ad, sports gambling ads, multiplayer online game ads, virtual ads, digital ads or virtual billboard ads or virtual ad through the use of digital technology to insert virtual advertising images on a virtual landscape or into a social network, social networking websites or third party websites or applications, a live or pre-recorded television show or video or sporting event and online or mobile coupons and promotions or offers for products or services, operating through credit cards or other payment services, automatically giving users discounts on their purchases at participating merchants, virtual or digital advertisements, banner ads, graphic color ads; promotions or offers inserted or overlays on images in a social network or website online or mobile device, social video sharing, video ad, audio-video & photography, near field communication (NFC), NFC boarding pass, mobile boarding pass, social shopping, sharing on a social networking system digital content, mobile social video sharing, virtual world ad, in-game advertising, mobile browser ad, mobile web ad, widgets or widget ad, bookmark ad, tabbed browsing ad, page zooming ad, ad-sponsored link, multiple platform website ads, interactive content marketing via a mobile device or other similar device or android device or tablet device or mobile internet devices or holographic devices or mercatot cell phones, (e.g. holographic phone) or other non-phone connected device or computer ads, stream search ad, communications, video or voice chat ad, floating ad, expanding ad, wallpaper ad, trick banner, pop-up, pop-under, map ad, mobile ads, mobile ad network, mobile advertising for mobile publishers and advertisers and mobile commerce, mobile location-based advertising and promotions or offers associated with location or maps in a social network or website online or mobile device.

The promotions may be an online promotion, which is any type of promotion or offer in any form provided over the Internet or World Wide Web, such as a social network or website, blog, pop up and the like, including mobile or wireless devices, as well as any Internet accessing device, including any type of computing device or computer.

The promotions may be mobile ad or mobile advertisement, which is a form of advertising via mobile or wireless device or electronic device or mobile devices or computer relating to mobile advertising through a mobile ad network, mobile advertising for mobile publishers and advertisers and mobile commerce, mobile location-based advertising and promotions or offers associated with location or maps in a social network or website online or mobile device.

The promotions may be online advertising, which is a form of promotion or offer that uses the Internet and World Wide Web to deliver marketing messages to attract customers. Examples of online advertising include contextual ads on search engine result pages, banner ads or graphic color ads, sponsored video ads, digital promotions or offers, online classified ads, yellow page ads, white page ads, text message ads, interactive advertising, post blogs, rich media ads, social networking ads, ad products for advertisers and users or members, interstitial ad, online classified advertising, advertising network, affiliate marketing and e-mail marketing, referral marketing, including e-mail spam. An advertisement server delivers many of these types of ads across the World Wide Web on a computer, mobile device or other devices.

The present invention may provide coupons, which is any of a ticket, a code or a document that can be exchanged for a financial discount or rebate when purchasing a product or service. Examples may include online coupons sent through emails, pop-up display coupons, a code sent to the individual's mobile device.

In some embodiments where the present invention comprising a mobile device for displaying information, advice, or guidance to the individual, the mobile device has an installed map service such as Google map, Yahoo map, and Mapquest. The map service has information about local businesses such as stores and service providers. The mobile device may, in addition to suggesting a product or a service, direct the individual to a local business where such product or service is available. In one embodiment, the mobile device is a smartphone where the information, advice, or guidance is based on the predicted wellness needs may be displayed and a local business related to the information, advice, or guidance may also be identified on the smartphone.

In some embodiments where the present invention comprises a mobile device for displaying information, advice, or guidance to the individual, the mobile device may be capable of receiving feedback from the individual, for example, about use of a suggested product or service. The feedback may be in the form of a ranking, or more specific comments. The feedback may be uploaded to a server where the feedback may be used to rank products or services. In addition, these rankings may be used by the present invention to provide future information, advice, or guidance on products and/or services to the individual.

In some embodiments, the information, advice, or guidance provided by the present invention is about nutrition and eating habits. Food groups may be generally divided into groups such as seafood, meat, seeds and nuts, dairy products, fruits, vegetables. The food groups may be further divided into sub-groups. For example, meat may be divided into white meat and red meat. Examples of red meat include beef, lamb, pork, and rabbit meat, while white meat includes chicken, turkey. The information, advice, or guidance on nutrition may be recommending a food group, or subgroup, or a specific food to an individual. The information, advice, or guidance on nutrition may also include one or more suggestions to stay away from certain food groups or subgroups or a specific food.

The nutritional information, advice, or guidance may also be information, advice, or guidance on daily limits on total number of calories, amount of fiber, proteins, sugar, salt, and bad fat (saturated fat and trans fat), or any other nutrients or ingredients, in grams or equivalent teaspoons or tablespoons and a total daily count indicator for each nutrient. The nutritional information, advice, or guidance may also be a rank-ordered list of suggestions for meal preparation and choices of food. In providing nutritional information, advice, or guidance, the individual's food allergy information, or any food contraindicated to the individual's medical conditions, a list of favorites, excluded, preferred, and non-preferred foods may be considered as personal preferences in the database 14.

In some embodiments, the present invention also considers the individual's personal preferences, in addition to the predicted wellness needs, to provide assistance to the individual. Such personal preferences may be collected from information about the individual's behavioral history, purchasing history, consumer history, psychological history, and/or psychiatric history. The individual or a person familiar with the individual (a guardian or caregiver) may input these personal preferences into a database 14 to be used for better providing assistance to the individual.

In some embodiments, the present invention also considers other additional information in predicting an individual's wellness needs. The additional information may include the individual's age, weight, height, body mass index, blood cholesterol level, race, ethnicity, social status, marital status, area of residence, occupation, education, allergies, diet, previous or present medications, medical history, family history of disease. This information may be entered into the database 14 by the individual, an assistant or a caregiver.

The correlations between the biological phenotypes and wellness needs are for providing guidance to an individual for assisting the individual's daily living. The relationships may, among other goals, provide a warnings to the individual for a risk of contracting a disease. The present invention may provide guidance to the individual for mitigating the risk to enhance wellness of the individual. The correlations of the present invention are not the same as diagnostics in the medical field, which are for identifying persons with a disease and the nature or cause of the disease based on measurement of a biomarker. One major difference is that diagnostics require a very low error rate and are regulated and monitored by U.S. Food and Drug Administration. Since the present invention aims at providing guidance to an individual for assisting the individual's daily living and does not provide medical treatments or therapies to the individual, it can potentially to tolerate higher error rate than diagnostics.

Furthermore, diagnostics are based on detecting a measurement of biomarker outside of a normal range. For example, the concentration of a biomarker in a sample is abnormally low or abnormally high, which indicates existing of a disease for an individual. On the other hand, the biological phenotype of the present invention is based on measurements of biomarkers in a range that also include normal range. Thus, the present invention provides guidance to an individual based measurements that may be in one or both of normal and/or abnormal ranges.

Figure 2:
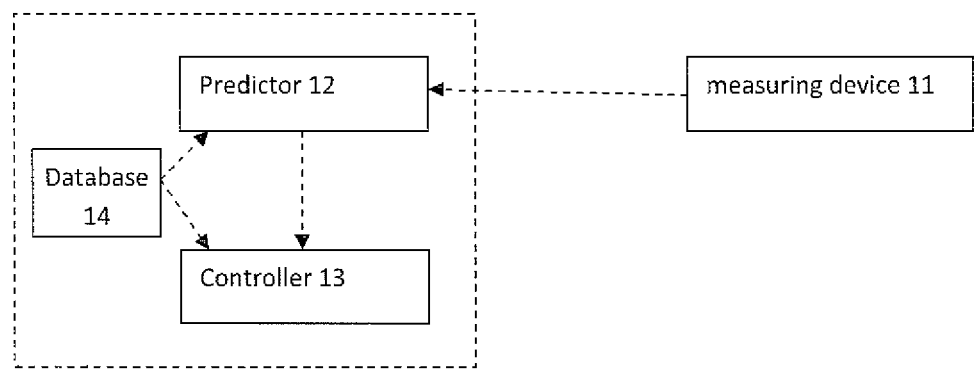
FIG. 2 is a diagram showing a system for providing assistance to an individual according to one embodiment of the present invention.

In another aspect, the present invention provides a system for providing assistance to an individual for maintaining or improving the individual's wellness, comprising a measuring device 11 for measuring a presence and/or concentration of one or more biomarkers in a sample from the individual, a predictor 12 for predicting a wellness need of the individual to maintain or improve the individual's wellness based on the measured presence and/or concentration of the one or more biomarkers where the one or more biomarkers are indicators of the wellness need, a controller 13 for altering the living environment of the individual or providing information, advice, or guidance to the individual addressing the wellness need of the individual, and a database 14 for storing links from biomarkers to diseases or health concerns to wellness needs (FIG. 2). The dotted lines indicate that the communication between components of the system may be wireless or hardwired. The dotted box indicates that, in some embodiments, the predictor 12, controller 13 and database 14 may be integrated into a single apparatus.

The measuring device 11 may be a biosensor, an electrode, or any other device that can measure the presence and/or concentration of a biomarker in the sample as described above. In some embodiments, the measuring device 11 has multiple biosensors/electrodes for parallel measurement of multiple biomarkers in the sample. In some embodiments, the measuring device 11 is a miniature device that may be easily carried by the individual for passive, continuous measuring while the individual carries out his or her daily life. The miniature measuring device may even be implanted inside the body of the individual, for example, as part of an artificial tooth, part of a stent in human cardiovascular systems, part of a stent in urine passages, or implanted in a nasal cavity or gastrointestinal tract, or uterus. The measuring device 11 may also be attached to the skin as a patch or strapped onto the skin.

The measuring device 11 is preferably in frequent contact with a sample from the individual. The sample may be measured in situ, such as by a measuring device 11 located in the mouth for measuring biomarkers in saliva, or implanted in blood vessel or urine passage for measuring biomarkers in blood or urine, respectively. The sample may alternatively be collected from the individual and then exposed to the measuring device 11 for ex situ measurement.

In some embodiments, there is a supplemental measuring device for measuring the physiological phenotype of the individual. The physiological phenotype may include physiological parameters such as body temperature, pulse rate, blood pressure, respiratory rate, hydration status, electromuscular activity and the like. The physiological parameters may be used to supplement the biomarker information in predicting the individual's wellness needs.

In some embodiments, a supplemental measuring or data collection device may collect data from the location (map) such as time at the location and any orthogonal data from the location such as, but not limited to, temperature, altitude noise, altitude, wind, humidity, pollution, oxygen, sunshine, pollen, crowd density, concrete, grass, night, day, near highway and traffic density at that time, aircraft flying, cosmic radiation levels, radon exposure, clothing and physiological conditions. Thus, in these embodiments, other data is collected and saved in addition to measurement of one or more biomarkers and/or physiological data so that such other data can be correlated with or used on conjunction with the biomarker data to predict one or more wellness needs.

In some embodiments, a ratio of between two biomarkers may be used in a correlation. A ratio between two biomarkers may better correlate with the one or more wellness needs, in comparison with a single biomarker.

A ratio between a biomarker and a product of a housekeeping gene may also be used in some embodiments. Housekeeping genes are typically constitutive genes that are required for the maintenance of basic cellular function, and are expressed in all cells of an organism under normal and patho-physiological conditions. Some housekeeping genes are expressed at relatively constant levels. Proteins expressed from these housekeeping genes, which are at relatively constant level, can be used as internal standard to which a biomarker is compared to and a ratio to the housekeeping gene product may be generated. More specifically, protein expression levels of housekeeping genes in a sample are determined, and used to compare relative protein expression levels of biomarkers, generating a ratio of biomarker to a housekeeping gene. Other constitutively expressed genes that are expressed at constant levels can also be employed.

In these embodiments, relative level of biomarkers (relative to a housekeeping gene or other constitutively expressed gene) in a sample may be determined, thus suggesting up regulation or down regulation of the biomarker in the sample. Up regulation and down regulation of biomarkers can reflect the biological condition in a way and to a precision not readily determined by relying on biomarker or DNA sequencing alone. This ratio can be maintained over any degree of sample dilution, and therefore can be used with a wide range of assays with varying sensitivities. This ratio approach can be particularly effective when measuring biological molecules in settings such as a toilet or urinal, where volumes of urine will vary with respect to volumes of water.

In some embodiments, the present invention may include correlation of biomarkers to a placebo effect. In medicine, the placebo effect is a positive therapeutic effect claimed by a patient after receiving a placebo believed by the patient to be an active drug. The "placebo effect" as used herein is a beneficial or detrimental effect measured in the biomolecules in an individual following a particular treatment, event, or circumstance that arises from the individual's expectations or beliefs concerning the treatment, event or circumstance rather than from the treatment, event or circumstance itself. In an embodiment of the present invention, the correlations of the present invention include correlations of biological molecules to a placebo effect, based on co-occurrence of the biological molecule and the placebo effect (such as the biological molecule present at the same time, receding or following the placebo effect). Such biological molecule may be called "placebo effect biomarkers" because the biological molecule may be present with a placebo effect. Presence of these "placebo effect biomarkers" can be indicators of belief enhancement. These biomarkers can then be used to assess activities and behaviors including eating specific foods or supplements, or combinations of activities to enhance these biomarkers in order to increase the placebo effect to improve the likelihood for a desired outcome. These "placebo effect biomarkers" may be also used as guidance for enhancement of an individual's belief, independently or in combination with other biomarker driven guides, to guide individuals or vendors.

The measurements are communicated to the predictor 12, which uses the measurements to predict a wellness need of the individual. The prediction is based on the presence and/or concentration of biomarkers for a disease or condition or health concern in a sample from the individual. Based on the information in the database 14, the biomarkers are linked to diseases or health concerns and thus to wellness needs associated with such diseases and/or health concerns. Thus, the system of the present invention provides assistance to the individual to satisfy a wellness need of the individual in order to maintain or improve the individual's wellness (e.g., preventing or mitigating the disease or health concern).

For example, elevated C-reactive protein in blood is a risk factor of depression. When an individual's blood level of the protein is elevated, then a signal may be sent, to alter the environment of the individual, the predictor 12 may predicts that the individual has wellness needs relating to preventing onset of an episode of depression or for reducing the severity of an episode of depression. More specifically, the wellness need may be one or more of the wellness needs discussed above in relation to depression.

The system may also comprise a database 14 that contains correlations between biomarkers and diseases or health concerns, as well as indications of wellness needs relating to such diseases or health concerns. The results of the biomarker measurements may also be saved in the database 14. The saved measurement results may be helpful to establish a reliable baseline for the particular biomarker in the sample of a particular individual. The increase or decrease of the biomarker in the sample can be more accurately determined when a reliable baseline is available and the system can learn to predict whether a more drastic intervention may be necessary in a particular case based on prior measurements.

The database 14 may also include the individual's preferences on behavior, choice of products, or choice of services. The preferences may be entered by the individual or an assistant/caregiver. Examples of the individual's preferences include a preference for biking over jogging, a preference for chocolate over cookies, a preference for rose scent over carnation scent, and a preference for a carbonated beverage over a juice. These personal preferences may help the system to better assist the individual's daily living by influencing the system in altering the individual's living environment or provision of information, advice, or guidance that considers the individual's preferences.

In some embodiments, the database 14 may also include other additional information that may be used in predicting an individual's wellness needs. The additional information may include the individual's age, weight, height, body mass index, blood cholesterol level, race, ethnicity, social status, marital status, area of residence, occupation, education, allergies, diet, previous or present medications, medical history, and family history of disease.

In some embodiments, the database 14 may also include data from the location (map), time at the location and any orthogonal data from the location such as, but not limited to, temperature, altitude noise, altitude, wind, humidity, pollution, oxygen, sunshine, pollen, crowd density, concrete, grass, night, day, near highway and traffic density at that time, aircraft flying, cosmic radiation levels, radon exposure, clothing and physiological conditions.

The database 14 of the present invention may evolve as more data is added into the database 14, and the information in the database 14 may also become more and more accurate and/or reliable over time due, for example, to the increase in the amount of data collected. As a result of this database 14 evolution, new correlations may be established and new ways of providing guidance to an individual may become possible. For example, uploaded biomarker data from an individual may be correlated with a map location, i.e., the location on map where the individual was when the biomarker data was measured or collected. Based on this relationship, and with more data and information available, the present invention may further correlate the map location with other information, such as environmental factors (such as pollen counts, UV intensity, etc). Therefore, the evolved database 14 may generate or include correlations from biomarkers to map location and environmental factors. In other words, different biomarkers may be correlated with different environmental factors. For example, a biomarker may be correlated with pollen count as "pollen biomarker." Another biomarker may be correlated with sunlight as "sunlight biomarker."

The database 14 may evolve even further as more new, different data are added. For example, the sunlight biomarker(s) might be correlated to different data such as increased skin sensitivity. If the system detects sunlight biomarker(s) in a sample from an individual, the system may then recommend to the individual to apply a skin care product for keeping the skin moisturized or protecting it from sunlight, or both. In another embodiment, the system can recommend to advertisers to sell to the individual suitable skin care products.

The prediction is then communicated to the controller 13. The controller 13 can alter the living environment of the individual or provide information, advice, or guidance to the individual based on the predicted wellness needs of the individual. For altering the living environment, the controller 13 may send a signal (wirelessly or through a wire connection) to effect the change of the individual's living environment. For example, a signal may be sent to a light switch to adjust the brightness or color of the lighting in the room where the individual is. In another example, a signal may be sent to a central air conditioning system to adjust the temperature, humidity.

The controller 13 may also transmit information, advice, or guidance to the individual through any suitable communication means such as a text message, a voice mail through a speaker, an email, a message displayed on TV or a computer screen, a message displayed on the screen of a handheld device, a voice message through a Bluetooth earphone, and/or a message to an assistant or a caregiver.

In some embodiments, the predictor 12 and controller 13 may be integrated into a single device with a microprocessor. The term "microprocessor" as used herein refers without limitation to a computer system or processor designed to perform arithmetic and logic operations using logic circuitry that responds to and processes the basic instructions that drive a computer. A typical processor comprises a single integrated circuit, or a few integrated circuits. Examples of microprocessors include those manufactured by Intel Corporation or Advanced Micro Devices (AMD), Inc.

The communication among the components of the system, e.g., measuring device 11, supplementary measuring device(s), predictor 12, and controller 13, may be conducted through wire connections or wireless signals. For example, the communication may use electrical, electronic, or electromagnetic signals, e.g., optical, radio frequency, digital, analog or other signaling scheme. The wireless communication is shown as dashed lines in FIG. 2.

The system of the present invention may be implemented in many devices. In some embodiments, the system has an implanted measuring device 11, which is periodically or continuously exposed to a bodily fluid of an individual. The measuring device 11 may be located in a stent in vascular system or in the urine passageway of the individual, in an artificial tooth, in a medical device implanted in the heart or an implant in the nose, for example. The measurements of one or more biomarkers in the bodily fluid may be transmitted wirelessly to a handheld device comprising a microprocessor. The handheld device may be a smartphone, a tablet device, a cell phone, a mobile internet device, a netbook, a notebook, a personal digital assistant, an internet phone, a holographic device, a holographic phone, a cable internet device, a satellite internet device, an internet television, a DSL internet device and a remote control.

The handheld device may contain both the predictor 12 and controller 13, which receives the measurements and predicts the individual's wellness needs. In these embodiments, the database 14 is also in the handheld device, e.g., on a RAM of the handheld device. The assistance to the individual may be transmitted in two ways. If the assistance is altering the living environment of the individual, the handheld device may send a signal to a device to for example, adjust the brightness or color of lighting, temperature, humidity, scent, the color of a wall, a furniture arrangement in the room or entire house, and/or play suitable music in the room or entire house. If the assistance is information, advice, or guidance to the individual, the information, advice, or guidance may be displayed on the screen of the handheld device. Any promotions or coupons relevant to the information, advice, or guidance may also be displayed or referenced on the screen of the handheld device.

Any device used for the measurement of biomarkers can be a device specifically designed for personalized monitoring (such as those devices described herein). Any assay for biomarker measurement may be personalized to an individual, but located in a shared device such as a toilet or a steering wheel, making the system a "personalized shared device".

In some embodiments, the system of the present invention is implemented in a toilet. The measuring device 11 is located in the toilet is exposed to urine and/or feces in the toilet bowl. The predictor 12 and controller 13 of the system may also be located in the toilet or at a remote location.

When an individual uses the toilet, urine and/or feces gets into the water. The biomarkers in the urine or feces will diffuse into the water for measurement by the measuring device 11. The measurements will then be communication to the predictor 12 which has access to a database 14, e.g., on a RAM.

In some embodiments, the toilet may also have a supplementary measuring device for determining physiological parameters of the individual such as the individual's body temperature, pulse rate and/or blood pressure. The predictor 12 predicts the individual's social wellness needs based on the measured biomarker(s) and optionally, any additional data such as physiological data and/or location data as discussed above.

The controller 13 based on the predicted wellness needs, provides assistance to the individual who just used the toilet. This assistance may be provided in any manner as discussed above or via any media or methodology discussed above.

In some embodiments, the system of the present invention is implemented in a urinal. The measuring device 11 is located in the urinal where it can be exposed to urine. The predictor 12 and controller 13 of the system may also be located in the urinal or at a remote location. When an individual uses the urinal, urine comes into contact with the measuring device 11. The biomarkers in the urine are measured by the measuring device 11. The remainder of the system is ad described above with reference to the embodiment carried out in a toilet.

In the case of a public toilet or urinal, a display device may be provided in association with the toilet or urinal to provide information, advice, or guidance or assistance to the individual that just used the urinal based on the predicted wellness needs. The information, advice, or guidance may alternatively transmitted through a wire or wirelessly to be broadcasted though a speaker, displayed on a wall or a projector screen, displayed on TV screen or computer screen, displayed on the screen gaming device, displayed on the screen of a handheld device (including smartphones, tablet computers, notebook computers, e-book readers, mobile internet devices, personal digital assistants, internet phones, holographic devices, holographic phones, cable internet devices, satellite internet devices, internet televisions, DSL internet devices and remote controls). Any promotions or coupons relevant to the information, advice, or guidance may also be displayed along with the information, advice, or guidance.

The urinal may also be operatively connected to a device to adjust the brightness or color of lighting, temperature, humidity, and scent in the room, the color of a wall, a furniture arrangement or play suitable music.

In some embodiments, the system of the present invention is implemented in a handheld device such as a smartphone, a tablet device, a cell phone, a mobile internet device, a netbook, a notebook, a personal digital assistant, an internet phone, a holographic device, a holographic phone, a cable internet device, a satellite internet device, an internet television, a DSL internet device and a remote control. The measuring device 11 in the handheld device is capable of being in direct contact with sweat on the skin of a hand for measuring the biomarkers in the sweat. The predictor 12, controller 13 and database 14 of the system may also be located in the handheld device, which has a microprocessor. When an individual holds the handheld device, the measuring device 11 comes into contact with the sweat of the individual. The biomarkers in the sweat may be measured by the measuring device 11. Optionally, the handheld device may have a supplementary measuring device for determining one or more physiological parameters such as the individual's body temperature, pulse rate and/or blood pressure. The handheld device may also use location data, time and/or environmental data collected by the device to assist the predictor 12 in making a suitable prediction.

The handheld device, based on the predicted wellness needs, may provide assistance and/or information, advice, or guidance to the individual who just used the handheld device in any manner or type as described above.

In some embodiments, the system of the present invention comprises an apparatus attached to a human body, such as an armband, wristband, waistband, a headband, a patch, socks, boots, shoes, glasses, a hairband, a headset, an earplug, a watch, a necklace, and a finger-ring. The attached apparatus may be carried or worn by an individual. The measuring device 11 is located in the apparatus and is configured for contact with a bodily fluid such as sweat on the skin of the individual for measuring one or more biomarkers. The predictor 12, controller 13 and database 14 of the system may also be located in the attached or worn apparatus, or in a device which has a microprocessor that is carried by the user or at some remote location. Optionally, the apparatus may have a supplementary measuring device for determining one or more physiological parameters of the individual such as body temperature, pulse rate and/or blood pressure. The apparatus may also use location data, time and/or environmental data collected by the device to assist the predictor 12 in making a suitable prediction. When the apparatus has a screen (such as watches, wristbands, armbands, waistbands, patches), the information, advice, or guidance may be displayed on the screen of the apparatus. Any promotions or coupons relevant to the information, advice, or guidance may also be displayed on or referenced by the screen of the apparatus. The information, advice, or guidance may also be broadcasted by a speaker of the apparatus.

In some alternative embodiments, the apparatus may not contain the predictor 12, controller 13 and database 14 of the system. This may be for example, when the apparatus is an earplug, hairband, necklace, or headset. In these alternative embodiments, the measurement results are transmitted to another device, such as a handheld device comprising a microprocessor.

In the embodiment where the apparatus are a pair of glasses, the glasses may also measure biomarkers in tears, in addition to biomarkers in sweat. The glasses may be capable of performing assays, and may operate without touching the eyes, to measure biomarker(s) in tears. Information, advice, or guidance may be displayed on the glasses or broadcasted by a speaker on the glasses.

In some embodiments, the system of the present invention comprises a device, which may come into direct contact with saliva of an individual. Such a device may be a dental hygiene device such as toothbrush, a dental brace, a dental flossing device or may be a device located in the mouth, such as an implant, artificial tooth or an attachment to a tooth. The measuring device 11 is included in the device. The measuring device 11 can measure one or more biomarkers in saliva. These measurements are transmitted to a device comprising a microprocessor for further processing as discussed above.

In some embodiments, the system of the present invention comprises a hair accessory, which may come into direct contact with the hair of an individual. The hair accessory may be a comb, a hair band, a headband a hair clip and the like. The measuring device 11 is included in the hair accessory and is capable of measuring one or more biomarkers in the hair of the individual. The measurements of the one or more biomarkers in the hair are transmitted to a device comprising a microprocessor and are processed as described above.

In some embodiments, the system of the present invention comprises a component in an automobile, such as a steering wheel. The measuring device 11 may be included in the automobile component and is capable of measuring biomarkers in the breath and/or sweat of an individual that is in the automobile, especially an individual operating the automobile. The measurements of the one or more biomarkers are transmitted to a device comprising a microprocessor and are processed as described above. The device may be used to adjust the environment in the automobile or provide information, advice, or guidance to the individual as discussed above. The device may also employ information collected by the automobile such as the travel time, information on eye movements of the individual, whether the lights or windshield wipers are in use, etc.

Each of the foregoing embodiments may be implemented with one or more supplementary measuring devices for determining one or more physiological parameters such as the individual's body temperature, pulse rate and/or blood pressure. These embodiments may also use location data, time and/or environmental data collected by the device to assist the predictor 12 in making a suitable prediction, as well as any other information available or collectable in the environment or surroundings where the device is employed.

In some embodiments, the system of the present invention may couple electronically or digitally to hospital, physician, nursing, or other medical staff communication system to enable the device to access the individual's recent medical history and prescribed medication, lab test results, consultation and information, advice, or guidance from physicians or nurses. Such information may help the system to better assist the individual in maintaining or improving wellness.

The method and system of the present invention are particularly useful in the fields of products such as electronic gadgets, music, food, fashion, games, books, and consumables, and services such as dating services, the pet services and supply industry, the political system, and travel industry.

The methods and systems of the present invention are particularly useful to provide information for the design, promotion and sale of better products and services related to wellness. Such products and/or services can be any product or service useful to improve wellness or assist an individual.

The methods and systems of the present invention are particularly useful for assisting product providers or services providers. For example, information from the present invention, such as biomarker correlation with consumer behavior, is useful in the promotion and/or selling of products or services related to wellness to individuals, including consumers, as well as in the design of customized or personalized products or services related to wellness, including consumer products and services.

Information can be provided to a product provider and/or a service provider and used in grading or rating of business, products or services related to wellness, for example a rating (for example of 1, 2, 3 or more levels) of quality or utility for a particular group of individuals, including consumers. Data can also be used by product providers or service providers to provide feedback or guidance related to wellness to individuals, including consumers.

It is to be understood, however, that even though numerous characteristics and advantages of the present invention have been set forth in the foregoing description, together with details of the structure and function of the invention, the disclosure is illustrative only, and changes may be made in detail, especially in matters of shape, size and arrangement of parts within the principles of the invention to the full extent indicated by the broad general meanings of the terms in which the appended claims are expressed.

What is claimed is:

1. A method for providing assistance for maintaining or improving an individual's wellness, comprising the steps of:
    measuring passively, without involvement of an operator, and recurringly, a presence and/or concentration of one or more biomarkers in a plurality of samples taken from the individual and stored in a database;
    predicting by a predictor a wellness need for maintaining or improving the individual's current wellness based on the measured presence and/or concentration of the one or more biomarkers, wherein the one or more biomarkers are indicators of a wellness need; and
    providing by a controller a real-time assistance to the individual within about one hour after the samples have been taken from the individual by addressing the wellness need of the individual, wherein the database, the predictor and the controller are connected through wire connection or wireless signals,
    wherein the real-time assistance is altering the living environment of the individual for addressing the wellness need of the individual, wherein the one or more biomarkers comprise a polypeptide.

2. The method of claim 1, wherein the one or more biomarkers further comprise polynucleotides, metabolites, microbes, inorganic compounds, or ions.

3. The method of claim 2, wherein the presence and/or concentration of the one or more biomarkers is measured by using recognition molecules selected from antibodies, antigens, aptamers, natural receptors, synthetic receptors, ligands, enzymes, enzymatic substrates, and nuclei acid probes.

4. The method of claim 1, wherein the measuring step is carried out using one or more biosensors comprising a transducer selected from optical transducers, mass-based transducers, magnetic field based transducers, electrochemical transducers, and calorimetric transducers.

5. The method of claim 1, wherein the presence and/or concentration of one or more biomarkers in the plurality of samples is measured by one or more electrodes selected from potentiometric electrodes, amperometric electrodes and conductometric electrodes.

6. The method of claim 1, wherein the presence and/or concentration of one or more biomarkers is measured by an array of recognition molecules selected from antibodies, aptamers, oligonucleotides and combinations thereof.

7. The method of claim 1, wherein the measuring step further comprises measuring a physiological parameter of the individual selected from body temperature, pulse rate, blood pressure, respiratory rate, hydration status, electromuscular activity, eye movement and combinations thereof.

8. The method of claim 1, wherein data measured in said measuring step is correlated with location data associated with a location wherein said measurement is made.

9. The method of claim 8, wherein the location data is data associated with the location selected from temperature, altitude noise, altitude, wind, humidity, pollution, oxygen, sunshine, pollen, crowd density, concrete, grass, night, day, near highway and traffic density at that time, aircraft flying, cosmic radiation levels, radon exposure, clothing and combinations thereof.

10. The method of claim 1, wherein the providing step comprises altering the living environment of the individual selected from adjusting brightness and/or color of lighting, adjusting room temperature, adjusting humidity, rearranging furniture, playing music, adjusting a volume of music or audio, changing a TV channel, playing a recorded voice or sound, changing an appearance of a wall or screen, retracting a roof, opening or closing a window, adjusting oxygen concentration in air, adding or adjusting a scent in air, introducing one or more air-borne chemicals into air and altering one or more of a display and web search results.

11. The method of claim 1, further comprising a step of providing information, advice, or guidance selected from a course of action for performing the predicted wellness need, a course of action for preventing or mitigating the predicted disease or health concern, a course of action for better coping with the predicted disease or health concern and combinations thereof.

12. The method of claim 1, further comprising a step of providing information, advice, or guidance comprises
suggesting one or more products selected from supplements, vitamins, beverages, beauty products, personal care products, weight loss products, skin care products, sports supplements, extracts, probiotics, seasonings, flavors, sweeteners, taste/aroma blockers/modifiers, bulking agents, video games, electronics, reading materials, music, movies, TV programs, live shows, apparel, accessories, footwear, home appliances, exercise equipment, types of food, boats, automobiles, bikes, restaurants, office supplies, furniture, and vacation resorts/destinations; and
suggesting one or more services selected from messaging, financial services, dating services, catering services, home cleaning services, home improvement services, hair dressing services, cosmetic services, professional counseling services, travel services, casino gaming services, shopping services, real estate services, sports-related services, entertainment services, online auction services and hospitality services; or suggesting at least one promotion or coupon for a product or service.

13. The method of claim 1, further comprising a step of suggesting a local business and/or providing a map location of a local business in relation to the information, advice, or guidance, wherein the information, advice, or guidance involves suggesting a product or a service, and the local business provides the suggested product or service.

14. The method of claim 1, wherein the measuring of the one or more biomarkers is performed with a measuring device which measures polypeptides in urine and the measuring device is located in a toilet.

15. The method of claim 1, further comprising a step of correlating a location where said measuring step is carried out with at least one environmental factor associated with said location.

16. The method of claim 15, wherein the environmental factor is data associated with the location selected from temperature, altitude noise, altitude, wind, humidity, pollution, oxygen, sunshine, pollen, crowd density, concrete, grass, night, day, near highway and traffic density at that time, aircraft flying, cosmic radiation levels, radon exposure, clothing and combinations thereof.

* * * * *